US011369591B2

(12) United States Patent
Jarrett et al.

(10) Patent No.: US 11,369,591 B2
(45) Date of Patent: Jun. 28, 2022

(54) DRUG DELIVERY FROM HYDROGELS

(71) Applicant: Incept, LLC, Lexington, MA (US)

(72) Inventors: Peter Jarrett, Lexington, MA (US); Rami El-Hayek, Norwood, MA (US); Timothy S. Jarrett, Cambridge, MA (US); Charles D. Blizzard, Westwood, MA (US); Amarpreet S. Sawhney, Lexington, MA (US)

(73) Assignee: Incept, LLC, Lexington, MA (US)

( * ) Notice: Subject to any disclaimer, the term of this patent is extended or adjusted under 35 U.S.C. 154(b) by 0 days.

(21) Appl. No.: 15/152,739

(22) Filed: May 12, 2016

(65) Prior Publication Data

US 2016/0331738 A1    Nov. 17, 2016

Related U.S. Application Data

(60) Provisional application No. 62/160,394, filed on May 12, 2015.

(51) Int. Cl.
| | | |
|---|---|---|
| *A01N 43/00* | (2006.01) | |
| *A01N 43/46* | (2006.01) | |
| *A61K 31/55* | (2006.01) | |
| *A61K 31/436* | (2006.01) | |
| *A61K 31/44* | (2006.01) | |
| *A61K 31/404* | (2006.01) | |
| *A61K 31/502* | (2006.01) | |
| *A61K 31/496* | (2006.01) | |
| *A61K 31/56* | (2006.01) | |
| *A61K 31/517* | (2006.01) | |
| *A61K 31/444* | (2006.01) | |
| *A61K 9/00* | (2006.01) | |

(52) U.S. Cl.
CPC .......... *A61K 31/436* (2013.01); *A61K 9/0048* (2013.01); *A61K 31/404* (2013.01); *A61K 31/44* (2013.01); *A61K 31/444* (2013.01); *A61K 31/496* (2013.01); *A61K 31/502* (2013.01); *A61K 31/517* (2013.01); *A61K 31/56* (2013.01)

(58) Field of Classification Search
None
See application file for complete search history.

(56) References Cited

U.S. PATENT DOCUMENTS

| | | | |
|---|---|---|---|
| 3,640,741 A | 2/1972 | Ztes | |
| 3,865,108 A | 2/1975 | Hartop | |
| 3,992,562 A | 11/1976 | Denzinger et al. | |
| 4,002,173 A | 1/1977 | Manning et al. | |
| 4,014,335 A | 3/1977 | Arnold | |
| 4,207,893 A | 6/1980 | Michaels | |
| 4,424,311 A | 1/1984 | Nagaoka et al. | |
| 4,741,872 A | 5/1988 | De Luca et al. | |
| 4,826,945 A | 5/1989 | Cohn et al. | |
| 4,853,224 A | 8/1989 | Wong | |
| 4,938,763 A | 7/1990 | Dunn et al. | |
| 5,100,992 A | 3/1992 | Cohn et al. | |
| 5,160,745 A | 11/1992 | De Luca et al. | |
| 5,292,362 A | 3/1994 | Bass et al. | |
| 5,304,595 A | 4/1994 | Rhee et al. | |
| 5,324,775 A | 6/1994 | Rhee et al. | |
| 5,410,016 A | 4/1995 | Hubbell et al. | |
| 5,510,418 A | 4/1996 | Rhee et al. | |
| 5,514,379 A | 5/1996 | Weissleder et al. | |
| 5,543,441 A | 8/1996 | Rhee et al. | |
| 5,567,435 A | 10/1996 | Hubbell et al. | |
| 5,573,934 A | 11/1996 | Hubbell et al. | |
| 5,587,175 A | 12/1996 | Viegas et al. | |
| 5,731,005 A | 3/1998 | Ottoboni et al. | |
| 5,752,974 A | 5/1998 | Rhee et al. | |
| 5,776,445 A | 7/1998 | Cohen et al. | |
| 5,844,016 A | 12/1998 | Sawhney et al. | |
| 5,849,035 A | 12/1998 | Pathak et al. | |
| 6,149,931 A | 11/2000 | Schwartz et al. | |
| 6,201,065 B1 | 3/2001 | Pathak et al. | |
| 6,214,966 B1 | 4/2001 | Harris | |
| 6,371,975 B2 | 4/2002 | Cruise et al. | |
| 6,413,539 B1 | 7/2002 | Shalaby | |
| 6,458,889 B1 | 10/2002 | Trollsas et al. | |
| 6,534,591 B2 | 3/2003 | Rhee et al. | |

(Continued)

FOREIGN PATENT DOCUMENTS

| | | |
|---|---|---|
| WO | 2006031358 | 3/2006 |
| WO | 2006031388 | 3/2006 |

(Continued)

OTHER PUBLICATIONS

Amsden "Solute Diffusion Within Hydrogels. Mechanisms and Models", Macromolecules, vol. 31:18382-8395 (May 13, 1998).
Gao et al., "PLGA-PEG-PLGA Hydrogel For Ocular Drug Delivery Of Dexamethasone Acetate", Drug Development And Industrial Pharmacy, vol. 36(10):1131-1138 (2010).
Liu et al., "Study Of An Alginate/HPMC-Based In Situ Gelling Ophthalmic Delivery System For Gatifloxacin", International Journal of Pharmaceutics, vol. 315:12-17 (2006).
Lou et al., "Drug release characteristics of phase separation pHEMA sponge materials", Biomaterials, 25:5071-5080 (2004).

(Continued)

*Primary Examiner* — Layla Soroush
(74) *Attorney, Agent, or Firm* — Christensen, Fonder, Dardi & Herbert PLLC; Peter S. Dardi; Diane E. Bennett

(57) ABSTRACT

Drug delivery involving hydrogels as used for various medical conditions, and includes hydrogels formed in an eye with extended drug release times. An embodiment of the invention is a method of delivering a therapeutic agent to a tissue comprising forming a hydrogel in situ in an eye with a therapeutic agent dispersed in the hydrogel, the agent having a low solubility in water. The agent may be essentially insoluble in water. The hydrogel may be made so that 50% to 100% w/w of the agent is released when the hydrogel is from 100% to 50% persistent, with the persistence being a measure of the dry weight of the hydrogel relative to an initial dry weight of the hydrogel.

21 Claims, 13 Drawing Sheets

(56) References Cited

U.S. PATENT DOCUMENTS

| | | |
|---|---|---|
| 6,579,519 B2 | 6/2003 | Maitra et al. |
| 6,632,457 B1 | 10/2003 | Sawhney |
| 6,747,090 B2 | 6/2004 | DeGroot et al. |
| 6,905,700 B2 | 6/2005 | Won et al. |
| 6,958,212 B1 | 10/2005 | Hubbell et al. |
| 7,129,210 B2 | 10/2006 | Lowinger et al. |
| 8,003,705 B2 | 8/2011 | Sawhney et al. |
| 8,383,161 B2 | 2/2013 | Campbell et al. |
| 8,409,606 B2 | 4/2013 | Sawhney et al. |
| 9,205,150 B2 | 12/2015 | Jarrett et al. |
| 9,254,267 B2 | 2/2016 | Sawhney |
| 9,370,485 B2 | 6/2016 | Sawhney et al. |
| 2003/0175324 A1 | 9/2003 | Robinson et al. |
| 2004/0076602 A1 | 4/2004 | Harris |
| 2004/0086479 A1 | 5/2004 | Grinstaff et al. |
| 2004/0131582 A1 | 7/2004 | Grinstaff et al. |
| 2005/0256065 A1 | 11/2005 | Harris et al. |
| 2005/0277864 A1 | 12/2005 | Haffner et al. |
| 2007/0233240 A1 | 10/2007 | Frank et al. |
| 2008/0241223 A1 | 10/2008 | Nivaggioli et al. |
| 2009/0017097 A1 | 1/2009 | Sawhney et al. |
| 2009/0252781 A1 | 10/2009 | Sawhney et al. |
| 2010/0104654 A1 | 4/2010 | Robinson et al. |
| 2010/0158980 A1 | 6/2010 | Kopczynski et al. |
| 2011/0142936 A1 | 6/2011 | Campbell et al. |
| 2011/0189291 A1 | 8/2011 | Yang et al. |
| 2012/0071865 A1 | 3/2012 | Jarrett et al. |
| 2013/0071462 A1 | 3/2013 | Jarrett et al. |
| 2013/0116341 A1 | 5/2013 | Askar et al. |
| 2013/0172268 A1 | 7/2013 | Jarrett et al. |
| 2016/0166504 A1 | 6/2016 | Jarrett et al. |

FOREIGN PATENT DOCUMENTS

| | | |
|---|---|---|
| WO | 2007001926 | 1/2007 |
| WO | 2007005249 | 1/2007 |
| WO | 2014138085 | 9/2014 |
| WO | 2016060925 | 4/2016 |

OTHER PUBLICATIONS

Siepmann et al., "Modeling Of Drug Release From Delivery Systems Based On Hydroxypropyl Methylcellulose (HPMC)", Advanced Drug Delivery Reviews, vol. 48:139-157 (2001).

Yasukawa et al., "Biodegrable Scleral Plugs For Vitreoretinal Drug Delivery", Advanced Drug Delivery Review, vol. 52:25-36 (2001).

Kernt et al., "Axitinib Modulates Hypoxia-Induced Blood-Retina Barrier Permeability And Expression Of Growth Factors", Growth Factors, 13 Pages (2011).

Vermonden et al., "Hydrogels For Protein Delivery", Chemical Reviews, vol. 112:2853-2888 (2012).

Zarzycki et al., "Drug Release From Hydrogel Matrices", Ecological Chemistry And Engineering, vol. 17(2) 117-136 (2010).

Al-Aswad, "Another Role for Avastin? Neovascular Glaucoma", Review of Ophthalmology, 5 Pages (Jun. 13, 2006).

Jain et al., "Lessons from Phase III Clinical Trials on Anti-VEGF Therapy for Cancer", Nature Clinical Practice Oneology, vol. 3(1):24-40 (Jan. 2006).

Office Action from Corresponding European Patent Application No. 16793509.7 dated Oct. 23, 2020, 10 pages.

Decision of Rejection from Corresponding Japanese Patent Application No. 2017-559083 dated Jan. 12, 2021, 2 pages.

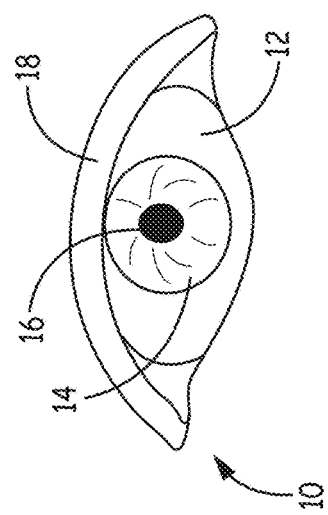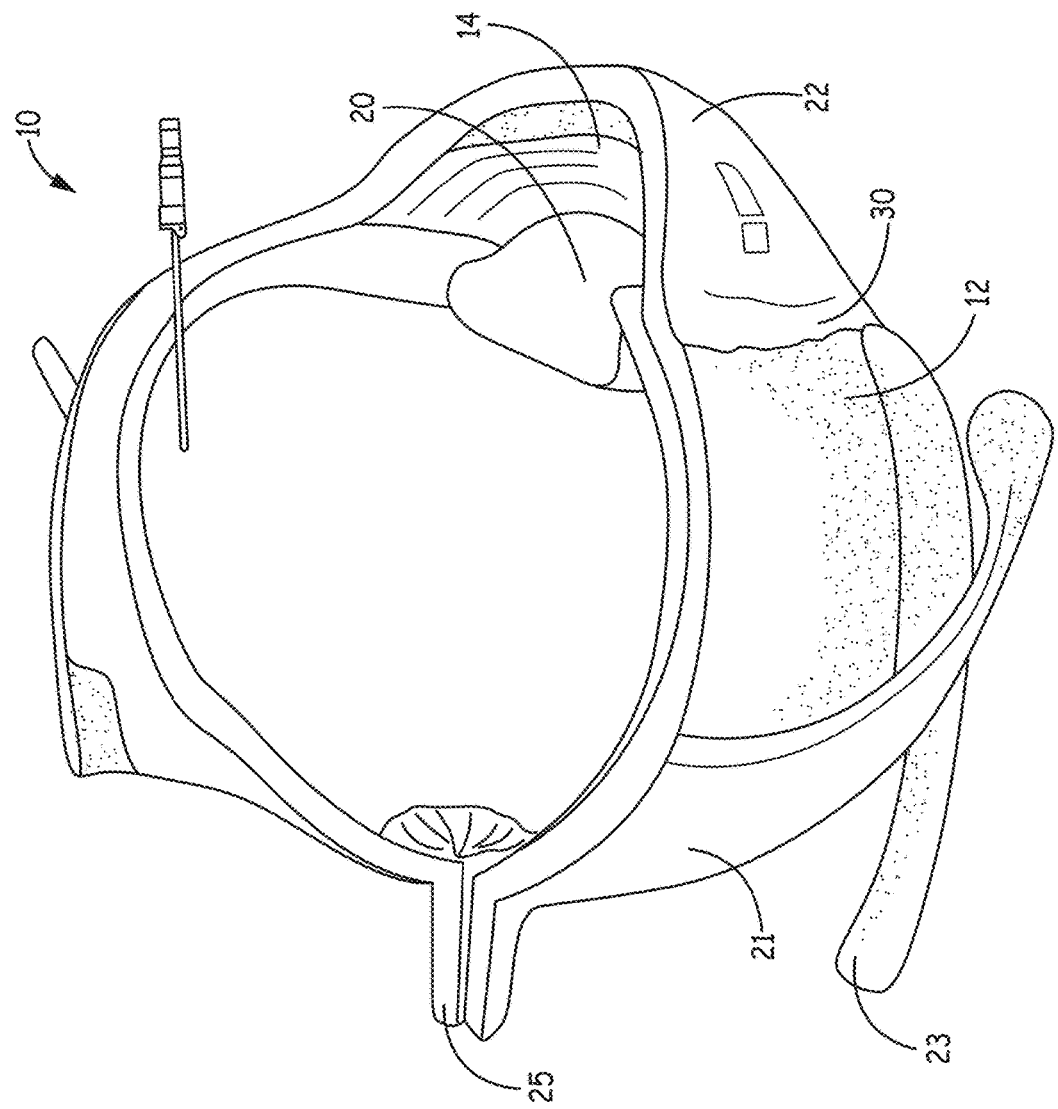

RELEASE AGENT FROM PERSISTENT HYDROGEL

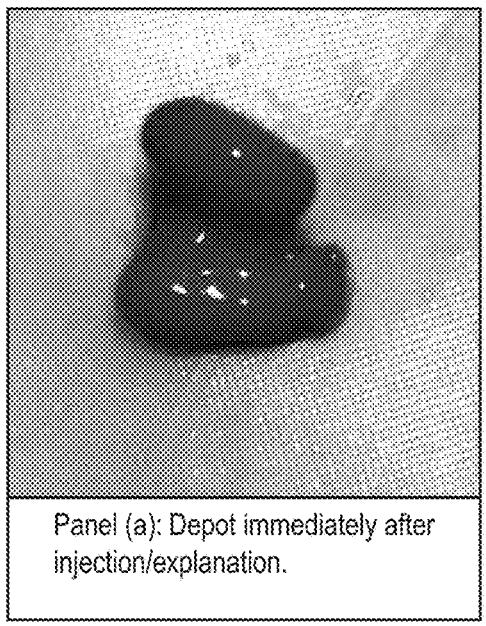

Panel (a): Depot immediately after injection/explanation.

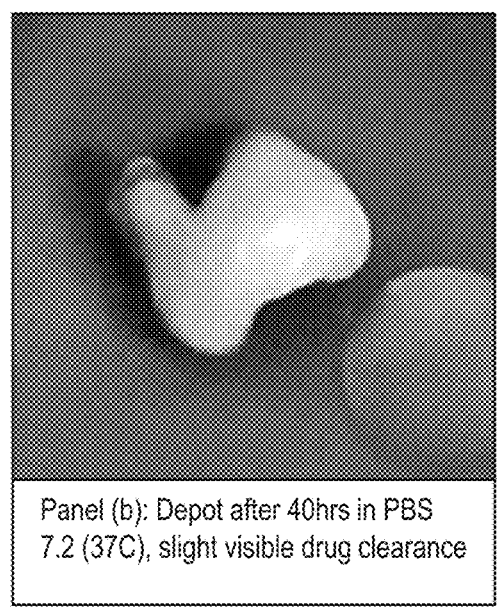

Panel (b): Depot after 40hrs in PBS 7.2 (37C), slight visible drug clearance

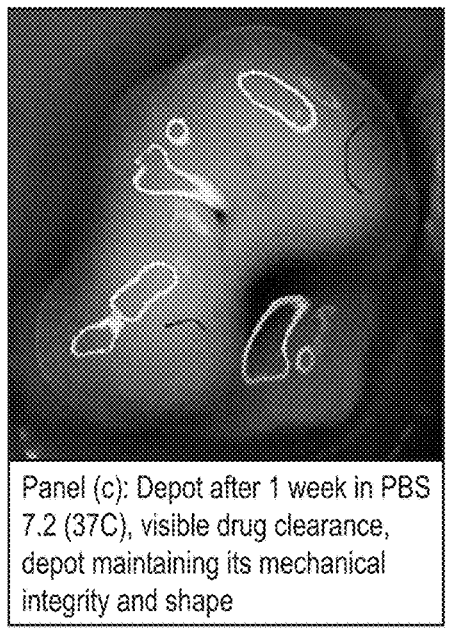

Panel (c): Depot after 1 week in PBS 7.2 (37C), visible drug clearance, depot maintaining its mechanical integrity and shape

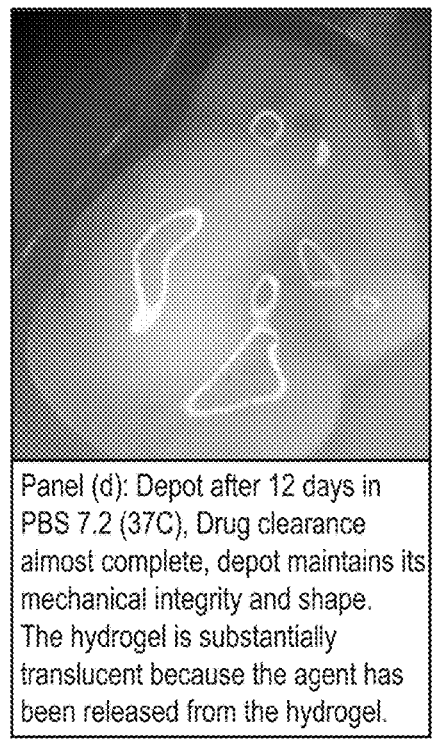

Panel (d): Depot after 12 days in PBS 7.2 (37C), Drug clearance almost complete, depot maintains its mechanical integrity and shape. The hydrogel is substantially translucent because the agent has been released from the hydrogel.

Steroid agent entrapped within the 9% PEG hydrogel network.

FIG. 9

Steroid release profile of neat steroid in media compared to that entrapped with the hydrogel depots.

Visual representation of flunisolide drug release from the hydrogel depot over time showing drug clearance over time.

Example of zone clearance from loteprednol etabonate hydrogel depots in release media.

Example of zone clearance from prednisolone hydrogel depots in release media.

Example of zone clearance from dexamethasone hydrogel depots in release media over time.

Example of zone clearance of steroids from hydrogel depots in release media visually correlates with drug solubility in release media over time.
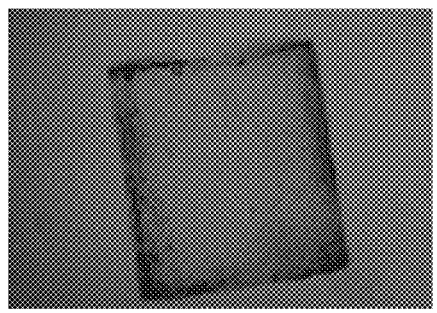
A. Prednisolone: Day 2
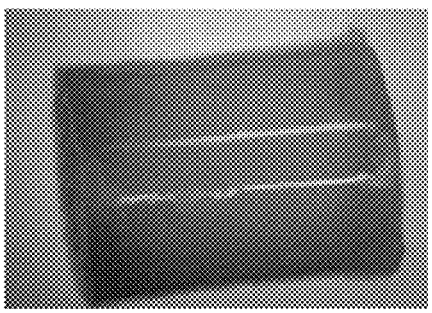
B. Prednisolone Acetate: Day 10
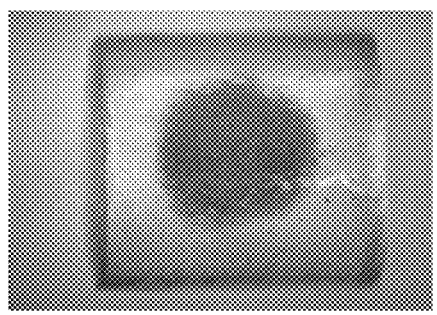
C. Dexamethasone: Day 10
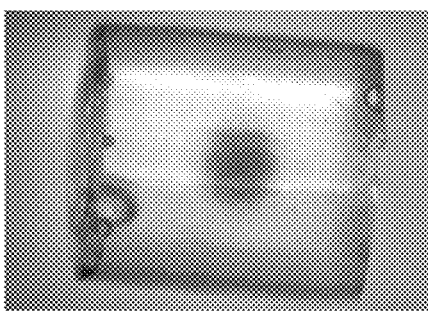
D. Micronized Dexamethasone: Day 10
FIG. 16

DRUG DELIVERY FROM HYDROGELS

CROSS REFERENCE TO RELATED APPLICATIONS

This application claims priority to U.S. Provisional Application No. 62/160,394, filed May 12, 2015, which is hereby incorporated by reference herein.

TECHNICAL FIELD

The technical field, in general, relates to drug delivery involving hydrogels as used for various medical conditions, and includes hydrogels formed in an eye with extended drug release times.

BACKGROUND

Age-related macular degeneration (AMD), diabetic retinopathy, diabetic macular edema (DME) posterior uveitis, choroidal neovascularization (CNV) and cystoid macular edema (CME) are sight-threatening back-of-the-eye diseases. Age related macular degeneration and diabetic retinopathy are significant causes of visual impairment in the United States and elsewhere; these conditions are generally caused by angiogenesis (unwanted blood-vessel growth in the eye) that damages the retina and ultimately can cause blindness. Posterior uveitis is a chronic inflammatory condition that causes about ten percent of the blindness in the United States.

SUMMARY

One invention disclosed herein is a crosslinked hydrogel formed in situ that releases a therapeutic agent that can be used, e.g., to treat back-of-the eye diseases. In this embodiment, aqueous polymeric precursor(s) are combined in flowable concentrations/viscosities with an agent and injected through a small gauge needle into the eye, where the precursor(s) form a crosslinked in situ hydrogel that releases the drug over time. The hydrogel may be formulated to adhere to itself or a tissue in or around the eye to enhance drug release effects and stability, to degrade to biocompatible components without causing inflammation, and to crosslink in place. A shape-stable hydrogel thus formed can effectively deliver the agent and advantageously have a well-controlled size, shape, and surface area. The hydrogels can be made to degrade after release of the drug.

BRIEF DESCRIPTION OF THE DRAWINGS

FIG. 1 depicts anatomical features of an eye from a frontal view;

FIG. 2 is a partially cut-away perspective view of an eye;

FIG. 9 is a montage of photographs of an in situ formed hydrogel releasing an agent, shown immediately after placement in vivo (panel a), after 40 hours (panel b), 1 week (panel c) or 12 days (panel d) in physiological buffered saline (PBS);

FIG. 16 is a photomontage of various agents released from hydrogels for the indicated times, and is an example showing that zone clearance of agents from hydrogel depots in release media such as PBS visually correlates with drug solubility in release media over time.

DETAILED DESCRIPTION

Figure 3:
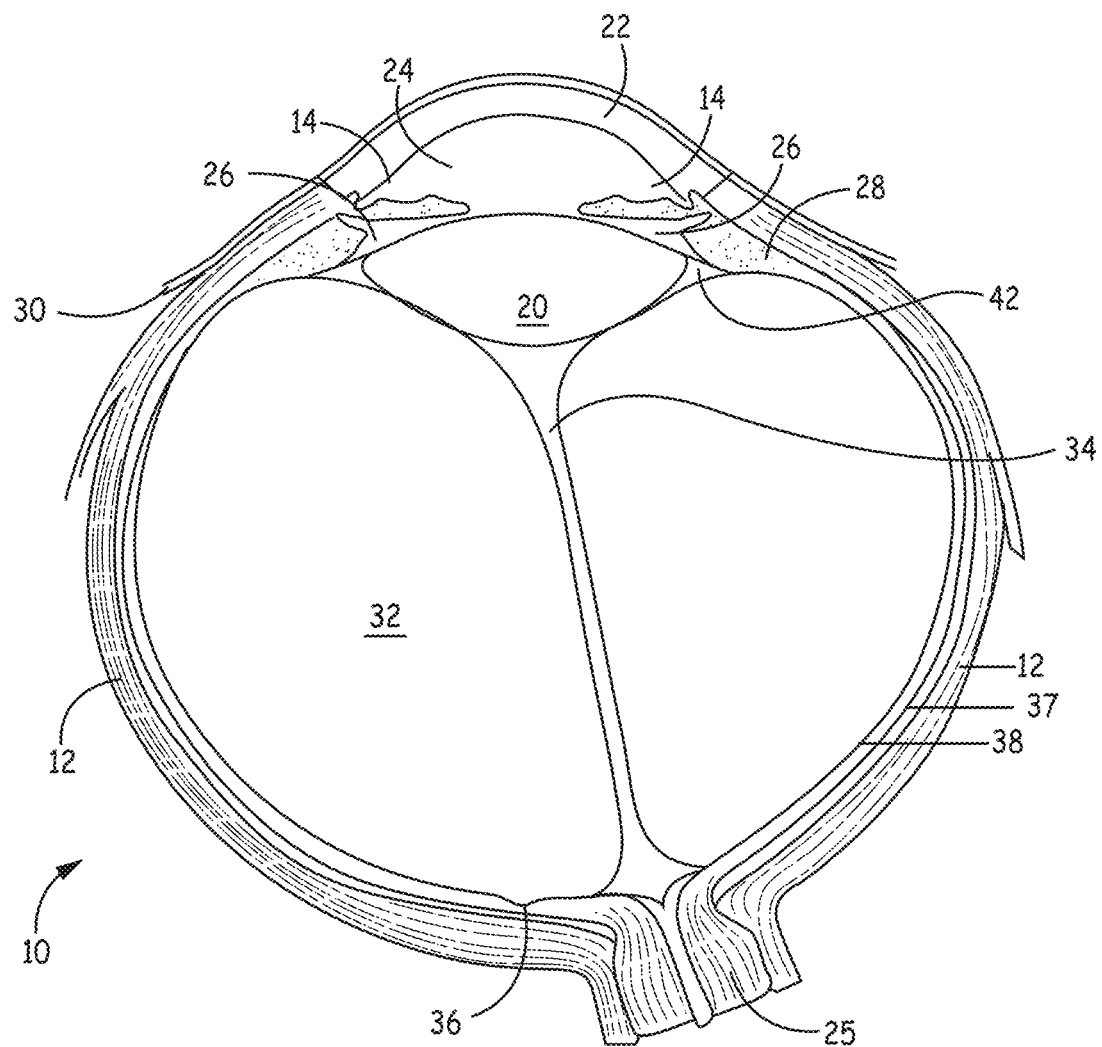
FIG. 3 is a cross-sectional view of an eye.

An embodiment of the invention is a method of drug delivery to a tissue, particularly an eye, comprising forming a hydrogel implant in situ with a therapeutic agent in the hydrogel (e.g., dissolved, suspended, dispersed throughout), the agent having a low solubility in water.

Drug delivery to the eye is an active field. Improvements in drugs for treatment of eye diseases have created new options for patients, including controlled release devices. One approach to ocular extended release was to put drugs into degradable particles that were injected into the eye. There were sometimes problems, however, with the particles settling onto the retina and causing contact toxicity. Others have created small drug delivery devices that are biodegradable rods of poly(lactic-co-glycolic acid) copolymers (PLA/PGA) that are impregnated with drugs and inserted into the eye. As they erode, the drug is able to move out of the PLA/PGA matrix, so that the degradation controls the rate of release. These devices provide extended release as they are eroded by the aqueous solution in the eye. Another approach has involved the use of certain hydrogels that are formed in situ, as in US 2009/0252781. While these were useful in certain situations, there are further techniques that can be used to improve biocompatibility and increase the range of clinical treatments that can be made with controlled release devices.

In particular, there are opportunities to use the properties of the agents, themselves, in combination with certain properties of the hydrogels to make depots (also referred to as implants) that release the agents over long periods of time in a controlled fashion to achieve an effective concentration without reaching toxic levels. A low solubility agent can go into solution particularly slowly in a hydrogel. The hydrogel can be made to readily allow diffusion without requiring degradation of the hydrogel (bioerosion) for release of the agent. The hydrogel's properties can be tailored to take advantage of the solubility of the agent to control release. Such properties can include a matrix structure that provides for diffusion of the agent without depending on bioerosion, a process of making the hydrogel that allows for dispersion of the agent in the hydrogel, and providing for the agent to be suspended as, e.g. micro and/or nano particles or droplets. The agent does not have to be encapsulated in particles, or otherwise combined with materials that need bioerosion to release them. Further, the hydrogels can be made to last longer than the agents they deliver so that delivery is controlled and the release of a final burst of the agent is kept within limits that avoid potentially toxic effects.

Some embodiments provide for encapsulation of agents in particles as an alternative or addition to non-encapsulated agents, particularly in areas outside the eye. The particles can be mixed with one or more precursors that form a hydrogel around them. Encapsulating particles are further discussed below.

In general, the eye presents an environment with competing design requirements. On the one hand, the volume of the eye is limited such that a large volume depot is disfavored. On the other hand, placing the depot in the eye, for instance by injection, involves some discomfort and trauma such that a large depot is helpful for minimizing the frequency of placement. Further, the eye is generally sensitive and placement of depots at locations that interfere with its requirements for effective vision points to making small depots. Moreover, therapeutic agents require a minimum concentration to be effective but may have toxic effects at concentrations that are too high. Therefore the agent must be released quickly and consistently enough to be effective without being released at too great a rate through the entire life of the implant. Use of a hydrogel around an agent presents the challenge of adding volume to the implant. In the case of a hydrogel that has internal space to allow for diffusion of agents, there are mechanical challenges to make an implant that resists mechanical forces applied to the eye such as rubbing the eyes or accidental application of force, or an elevated intraocular pressure present in some pathologies that are the target of the agent. An open, lightly crosslinked hydrogel structure tends to have more flexibility, but less mechanical strength compared to a relatively more closed hydrogel that has more closely spaced crosslinks.

But it is possible to use the small volume of the eye as an advantage instead of a disadvantage. A hydrogel that allows diffusion of an agent is affected not only by the concentration of the agent in the hydrogel but also by the concentration of the agent in the limited volume of the eye. A hydrogel depot with a relatively open matrix can be thus use the small volume of the eye as a parameter to control release because the amount of released agent can limit further release. The hydrogel structure, size, shape, loading, and choice of materials can thus be balanced, in combination with the properties of the agent, to provide an effective controlled release implant device. These various competing design features can, in fact, be reconciled to provide delivery of an effective concentration of an agent during a period of time, while avoiding toxic over-release of the agent.

In contrast to hydrogels that are permissive to agent diffusion, erodible hydrogels prevent diffusion until the matrix is eroded. Such designs have an advantage of directly controlling a rate of release of the agent. Since such designs have relatively densely crosslinked matrices, they can be made mechanically strong to resists mechanical forces involved in their implantation or after implantation, for example, by patients rubbing their eyes or receiving an accidental application of force, or stresses internal to the eye in some pathologies that are the target of the agent.

Locally formed hydrogels made in situ from precursors in aqueous solution can serve as depots of drugs or other therapeutic agents for ocular drug delivery, or delivery of agents at other sites. Described herein are hydrogels that can be formed in situ on a tissue or organ to deliver agents. The term on a tissue is broad, and includes contact with a tissue, in the tissue, around the tissue, in a tissue void or defect, in a potential space in the body, and so forth. An organ is a tissue. The term on an organ is broad and includes in the organ, on it, around it, and so forth. In situ refers to forming a material at the site where it is intended to be located. Thus a hydrogel may be formed in situ in a patient at the site wherein the hydrogel is intended to be used, e.g., as a drug depot for controlled release. Some drugs, such as some tyrosine kinase inhibitors (TKIs), have demonstrated corneal toxicity even in eye-drop form because the drugs are contacting the eye tissue directly. An advantage of the hydrogel is that the hydrogel shields the tissue from contact with the agent, e.g., as a solid particle or a suspended form. The agent is slowly released from the hydrogel in a diffuse form.

Figure 7:
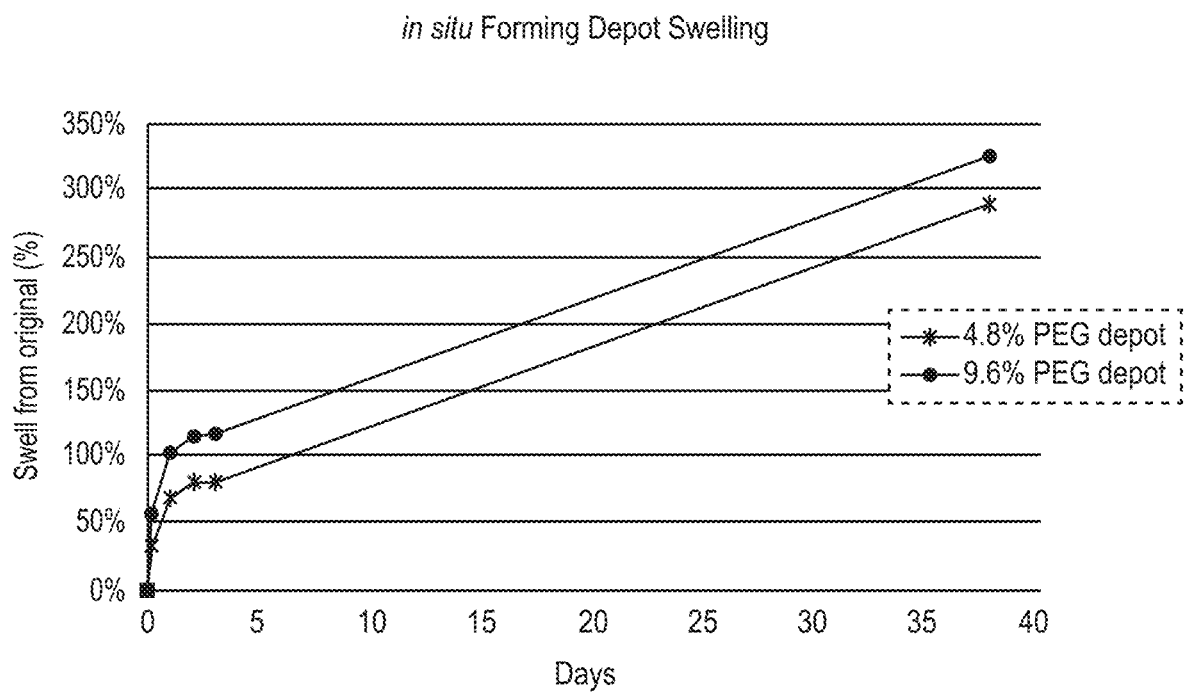
FIG. 7 is a plot of swelling of a hydrogel volume as it degrades without exterior constraints.
Figure 8:
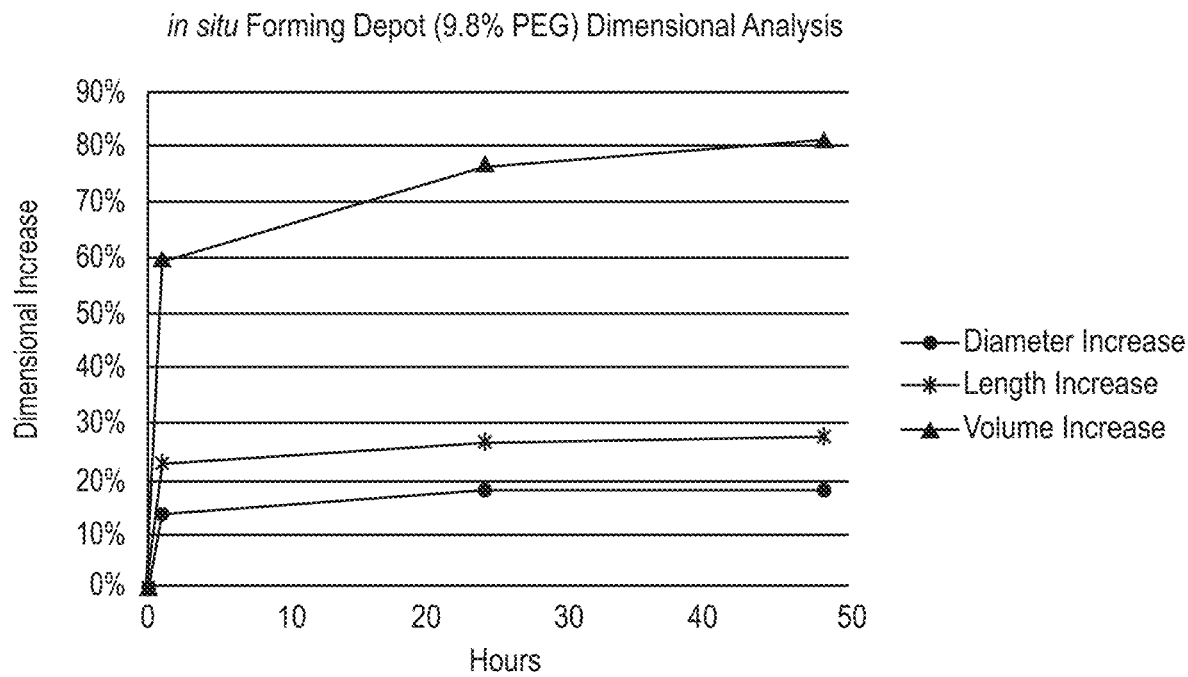
FIG. 8 is a plot of the dimensions of the hydrogel depot of FIG. 7.

Alternative embodiments include hydrogels formed outside the body and implanted into the body, e.g., intravitreally. Example 1 describes the swelling and persistence of two hydrogels made with a polyethylene glycol (PEG) matrix at a solids concentration of a 5% or 10% w/w PEG, see Table 3. The hydrogels were made from a first PEG precursor having an electrophilic end group (succinimidyl azelate, SAZ) and a second PEG precursor having nucleophilic end group (amine). The PEGs had 4 or 8 arms and a nominal molecular weight of 20 k each. They were combined in buffered solution in presence of a polysaccharide (hyaluronic acid, HA, at 1% w/w). The combination was found to have a low viscosity suited for injection through small bore needles and the resultant hydrogel matrix provided a structured that maintained its shape and mechanical integrity within a space gelation, e.g., intracameral, in a vitreous body, or other location. The precursors had good syringeability and good cohesion characteristics. The HA is a high molecular weight non-newtonian linear molecule; it enhanced viscosity of the precursor solution and performed well under high shear situations (passage through a thin gauge needle). A variety of different dilutions of 850 kDa HA were tested, with about 1% w/w providing a good result in this case. The buffers used to dissolve each precursor made a neutral pH when mixed, and the buffer with the SAZ precursor was of low pH in order to maintain stability of the polymer in solution (to avoid pre-hydrolysis). Each of these components, when mixed together, formed a hydrogel that maintained shape stability and volume stability, keeping its shape and position in a space until forming a hydrogel in 2-3 minutes. FIGS. 7 and 8 depict plots of swelling and dimensional change, respectively, for these hydrogel depots placed in vitro in physiological buffer solution (PBS). It was further observed that, as the hydrogels degraded, they continued to swell in a linear trend upwards to 1000% before liquefying. Most dimensional changes occur within the first hour. As the hydrogels degraded, they became mechanically more weak and swelled. These tests were conducted in an unrestrained area and, if formed in vivo, will swell minimally in vivo under conditions where surrounding mechanical forces limit swelling.

In Example 2, a hydrogel of the composition of Example 1 further comprising a small amount of fluorescein for visualization and the agent dexamethasone was formed in situ in an eye in a volume of about 25 µL. The depot was explanted and placed in an excess of PBS to observe release of the agent and persistence of the hydrogel. The agent was observed to be cleared from the hydrogel in inward direction, with the edges of the implant having the lowest concentration of the agent and the interior of the hydrogel having the highest concentration (FIG. 9). The hydrogel was essentially persistent during the observed time of 12 days and the visual observations were consistent with volumetric release and persistence data shown in plots herein. The hydrogel had a stable shape and consistent mechanical properties, based on manipulation of the hydrogel. Examples 3-8 provide detailed examples of making and using various hydrogels and agents. Example 9 is an example of how to make a kit for making hydrogels in vivo to release agents. Artisans can readily appreciate how to apply these Examples, and all the Examples more generally, to make and use hydrogels using the full range of precursors, agents, and sites of application set forth in other portions of this same disclosure.

Figure 10:
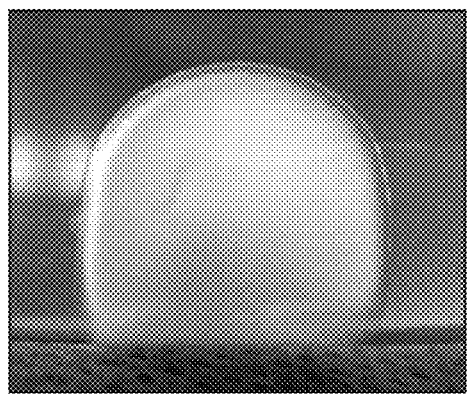
FIG. 10 is a photograph of a hydrogel implant with an agent entrapped in the implant for release, in a PBS.
Figure 11A:
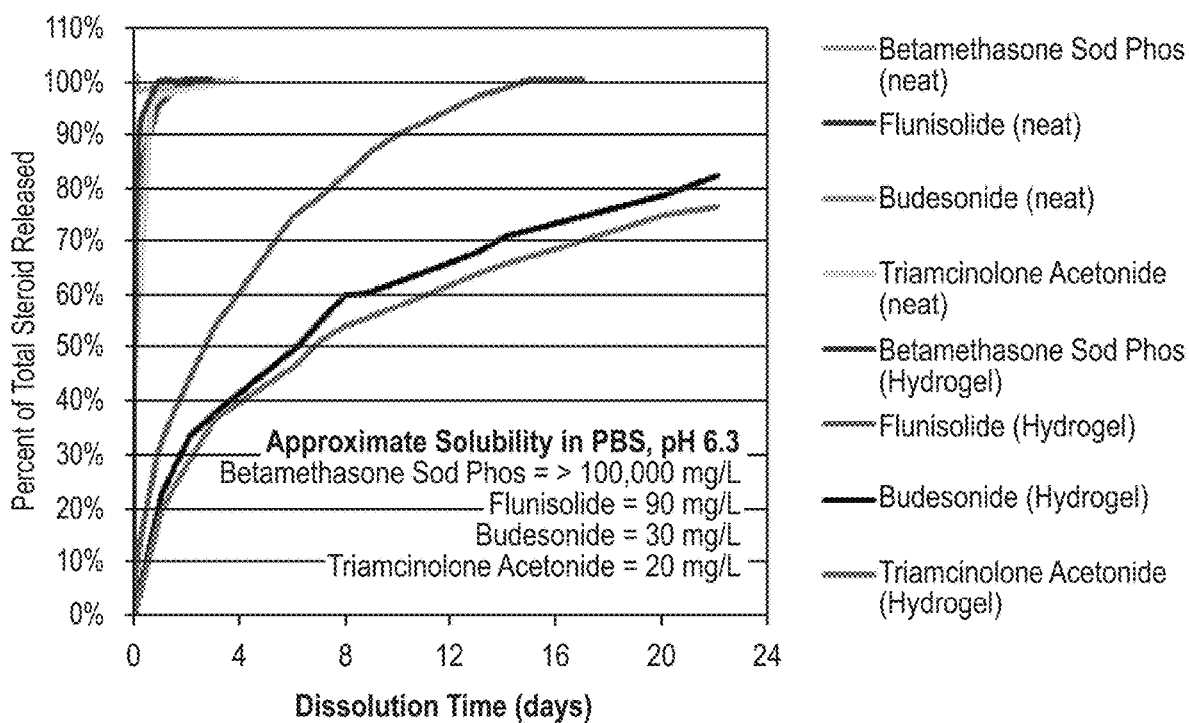
FIG. 11A is a plot of a release profile in PBS of agents entrapped in a hydrogel depot or as placed directly into the PBS.

Example 10 shows release profiles for a variety of exemplary agents, Flunisolide (solubility 90 µg/mL), Betamethasone Sodium Phosphate (freely soluble in water), Budesonide (30 µg/mL, and Triamcinolone Acetonide (20 µg/mL. These agents were placed into PBS or dispersed in a hydrogel (FIG. 10) placed into PBS, the hydrogel being made from a hydrophilic precursor (4-armed PEG) with electrophilic groups and a small hydrophilic precursor with nucleophilic groups (trilysine). The release rate from the agent-containing hydrogel depots was compared to the dissolution profile of the same amount of the agent in a neat formulation (FIG. 11A).

Figure 11B:
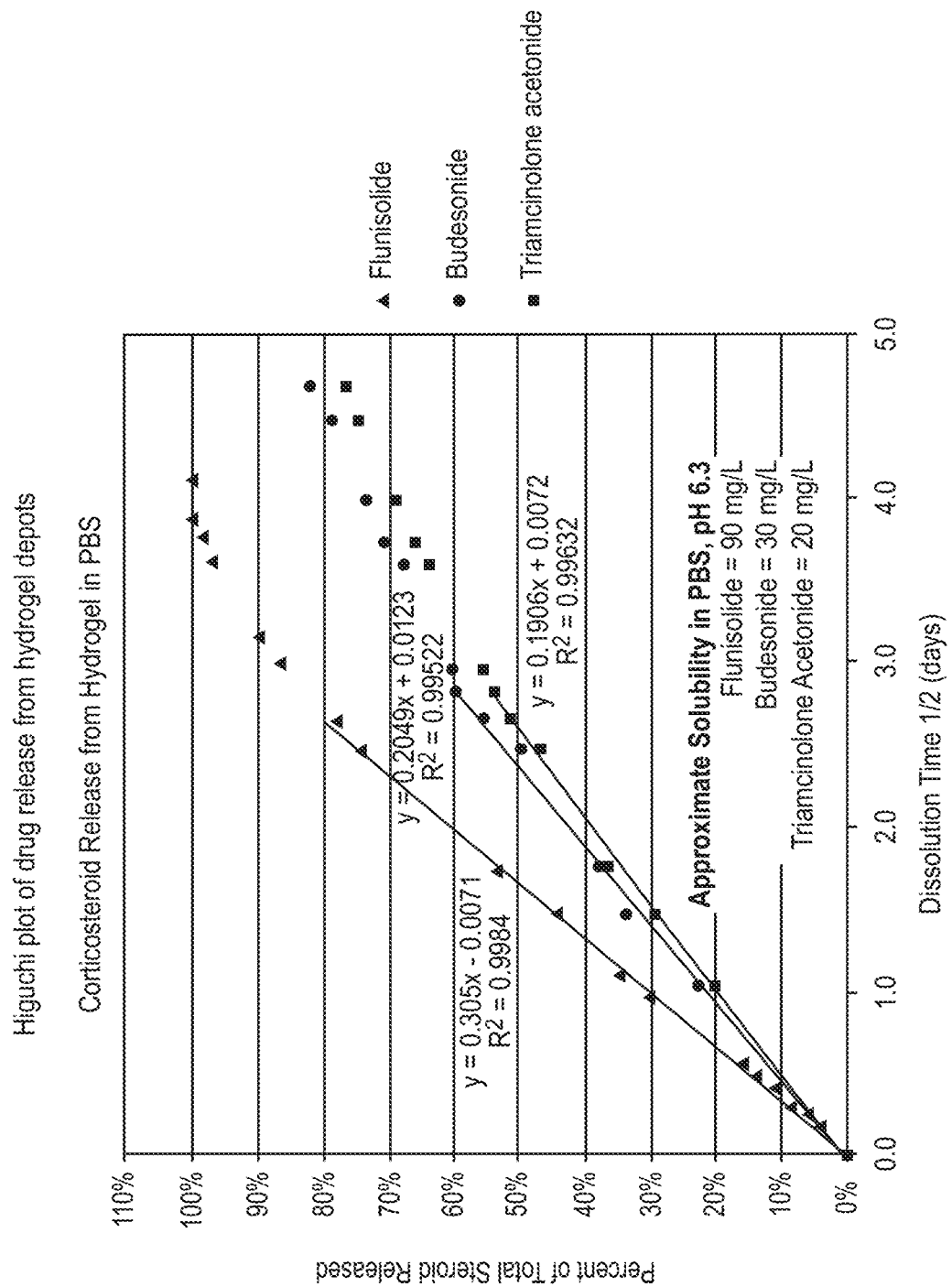
FIG. 11B is the plot of FIG. 11A presented as a Higuchi plot.
Figure 11C:
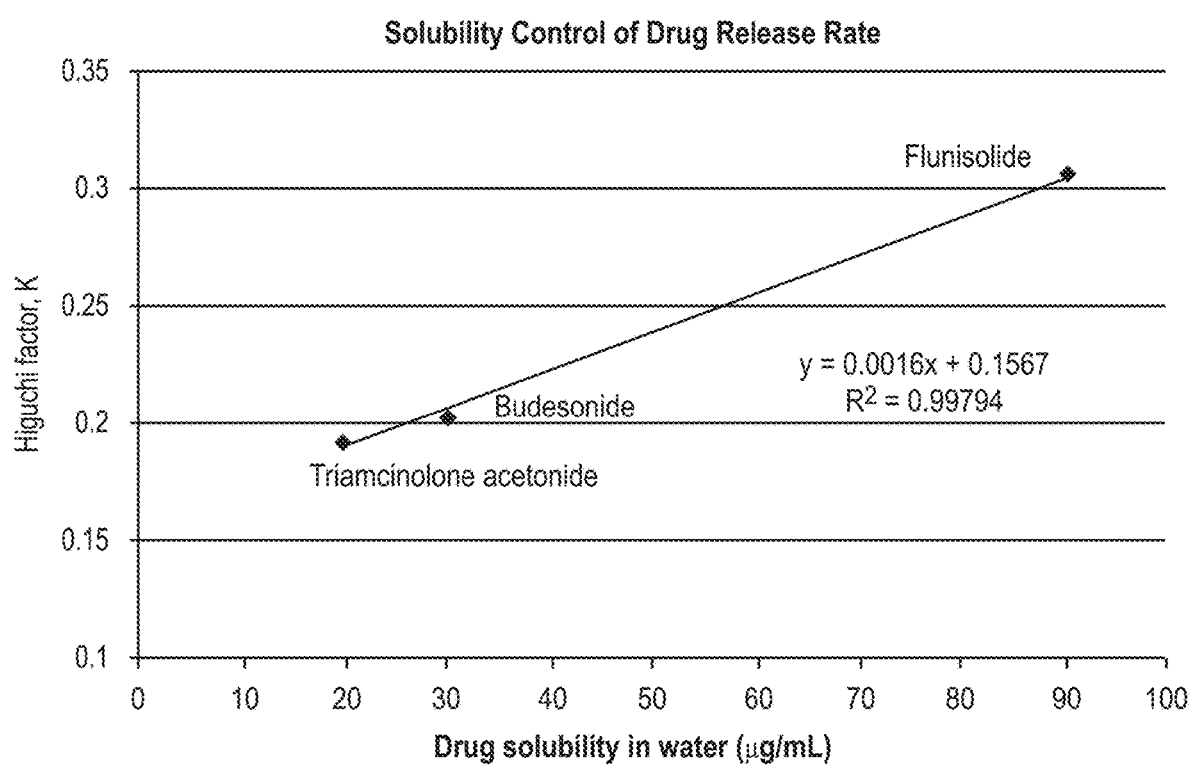
FIG. 11C is a representation of the data of FIG. 11A to show the Higuchi factor, K, as having a linear relationship with drug solubility for low or very low solubility agents released from the hydrogels.
Figure 12:
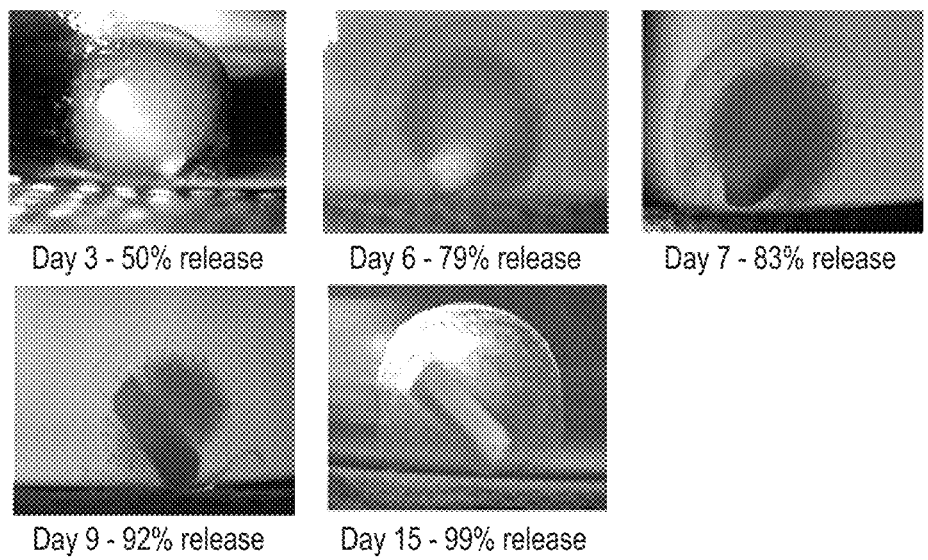
FIG. 12 is a photographic montage of a controlled release of an agent from a hydrogel depot showing clearance of the agent over time.
Figure 13:
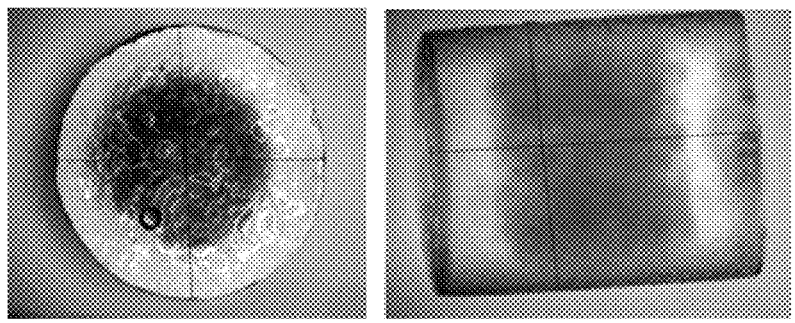
FIG. 13 is an example of zone clearance of loteprednol etabonate from a hydrogel depot in PBS.
Figure 14:
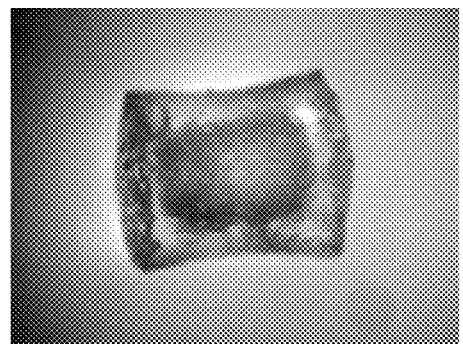
FIG. 14 is an example of zone clearance of prednisolone from a hydrogel depot in PBS.
Figure 15:
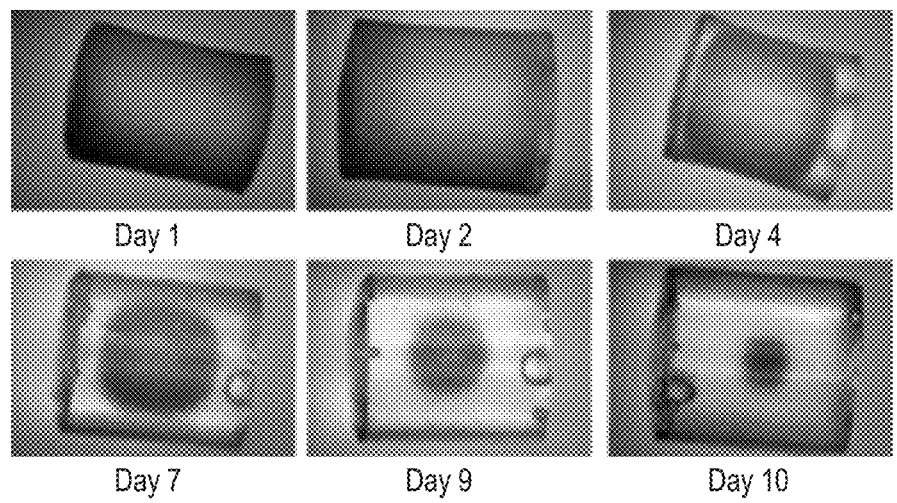
FIG. 15 is a photographic montage of a controlled release of dexamethasone from a hydrogel depot showing clearance of the agent over time.

FIGS. 11B and 11C are plots of the data of Example 10. FIG. 11B is a Higuchi plot showing that drug release versus square root of time is a linear relationship, with slopes (the slope is equal to the Higuchi factor, K) proportional to drug solubility, drug diffusivity, initial drug concentration, depot surface area, and other depot design factors. FIG. 11C shows the linear function of solubility relative to K, for the same initial drug concentrations and other depot design factors. A visual representation of drug release from the depots over time is presented in FIG. 12 for an exemplary agent (flunisolide). The results demonstrated that entrapment of an equal mass of agent within the confines of the hydrogel appreciably slowed the agents' release rate compared to freely dispersed agents in an equal volume of dissolution media, and that the tapered drug release profile correlated with drug solubility.

These data further establish the extended release rate from the in situ depots and model in vivo conditions. Injection of the pre-hydrogel material containing a suspension of exemplary agents (steroids) into the confines of the viscous vitreous was observed to create a spheroidal hydrogel depot at the injection site. These depot examples formed in vitro created a similar spheroidal hydrogel depot (e.g., FIG. 10). The drug release data from these in vitro formed depots allows prediction of the in vivo drug release rate. The Higuchi equation for release from this type of construct can be represented by the following (Siepmann, J.; Peppas, N. A. Modeling of Drug Release from Delivery Systems Based on Hydroxypropyl Methylcellulose (HPMC). Adv. Drug Deliv. Rev. 2012, 64, Supplement, 163-174):

$$M_t = A\sqrt{2C_0 D C_s t} \qquad \text{Equation 1}$$

Where $M_t$ is the mass of drug eluted at time t, A is the surface area, $C_0$ is the initial drug concentration, $C_s$ is the drug solubility, D is the diffusion coefficient. This equation assumes $C_0 \gg C_s$, edge effects are negligible, swelling or dissolution of the hydrogel depot is negligible, diffusivity is constant, temperature and pH are constant, and perfect sink conditions are maintained. More generally, the equation can be represented as $$M_t/M_\infty = k\sqrt{t} \qquad \text{Equation 2}$$

Where M∞ is the cumulative drug released at infinite time and k is a constant (Higuchi factor) reflecting the depot design variables. Thus, the drug or drug fraction release profile is tapered when plotted versus time, but linear when plotted versus the square root of time.

The release of the low solubility agent is thus regulated by the limited solubility of the agent in the physiological environment within the hydrogel and by the concentration gradient at the hydrogel interface with the physiological environment, which equals the drug solubility under perfect sink conditions. A tapered drug release profile is created as the front of the concentration gradient recedes from the interface. This retreating front can be observed as a gradually increasing clear zone at the periphery of the depot. Regulating the amount of low solubility agent within the depot can therefore control the duration of the drug release. The drug release rate from the depot in the vitreous is expected to be extended relative to an injection of unconstrained neat steroid in the vitreous thereby prolonging the duration of action of the drug within the eye. An additional benefit is that particles of drug are entrapped within the hydrogel, whereas migrating insoluble drug particles within the eye may result in an adverse tissue reaction or vision impairment when particles enter the visual axis. Factors expected to influence the rate of drug release from the in situ formed hydrogel depot include: drug solubility, drug particle (liquid or solid) size, common solubility factors (pH, temperature, salts, and so forth), drug amount within the depot creating differing concentrations and gradients, uniformity of drug within the depot, depot surface area, fluid turnover or exchange rate at the depot interface, hydrogel degradation and dissolution, depot additive agents (such as surfactants), and possibly other factors known to alter the solubility of an agent.

In a similar construct described in Example 11, various agents were suspended in hydrophilic hydrogel precursor solutions crosslinked and formed as cylindrical depots. The agent-suspended gels were removed from the tubing and ex vivo release was initiated in dissolution media. Zone clearance (steroid released) from the depot interface inward was observed and visually recorded. See FIGS. 13-16. A similar observation is expected to occur over time during in vivo drug release.

Examples 12-14 detail results of experiments testing potential toxicity of agents released in bursts. The hydrogel depots consistently release effective concentrations of the agents over a period of time. After that period of time, the hydrogel loses mechanical integrity and the matrix structure becomes loosely organized. If there is any remaining agent during this phase of degradation, the agent might be released more rapidly, or in a burst, such that the agent is at a concentration that is higher than what is needed for effectiveness or is, potentially, in a toxic amount with respect to local tissues. In vivo tests in eyes were conducted to measure the potential effects of a burst release to understand how much persistence would be necessary relative to the total volume and remaining volume of the agents. Considering the many design variables involved in the delivery process, some experimentation was needed to establish that the delivery processes described herein are suitable for the ocular space. The results show that the depots can be designed with a suitable persistence, loading, and other factors to effectively deliver drugs over a sustained period of time without falling short of the various design parameters.

The hydrogel depot is designed to provide an effective concentration of the agent at its site of intended use. The term effective amount or effective concentration or therapeutically effective/concentration refers to the amount of an agent that is sufficient to effect beneficial or desired results. The effective amount may vary depending upon one or more of: the subject and disease condition being treated, the weight and age of the subject, the severity of the disease condition, the manner of administration and the like, which can readily be determined by one of ordinary skill in the art. An effective concentration can be shown by pharmacodynamic effect. As an alternative, a calculated effective amount may be provided, meaning that 50-100 times the IC50 for the agent against the substrate; Artisans will immediately appreciate that all ranges and values between the explicitly stated bounds are contemplated, with, e.g., any of the following being available as an upper or lower limit: 50, 60, 70, 80, 90, or 100. IC50 refers to the Median Inhibition Concentration (concentration that reduces the effect by 50%), e.g., inhibition of the unwanted pathological effect.

Anatomy of the Eye

The structure of the mammalian eye can be divided into three main layers or tunics: the fibrous tunic, the vascular tunic, and the nervous tunic. The fibrous tunic, also known as the tunica fibrosa oculi, is the outer layer of the eyeball consisting of the cornea and sclera. The sclera is the supporting wall of the eye and gives the eye most of its white color. It extends from the cornea (the clear front section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. The conjunctiva effectively surrounds, covers, and adheres to the sclera. It is has cellular and connective tissue, is somewhat elastic, and can be removed, teased away, or otherwise taken down to expose a surface area of the sclera. The vascular tunic, also known as the tunica vasculosa oculi, is the middle vascularized layer which includes the iris, ciliary body, and choroid. The choroid contains blood vessels that supply the retinal cells with oxygen and remove the waste products of respiration.

The nervous tunic, also known as the tunica nervosa oculi, is the inner sensory which includes the retina. The retina contains the photosensitive rod and cone cells and associated neurons. The retina is a relatively smooth (but curved) layer. It does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

Light enters the eye, passes through the cornea, and into the first of two humors, the aqueous humour. Approximately two-thirds of the total eyes refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it: the vitreous humor, retina, and optic nerve. On the other side of the lens is the second humour, the vitreous humour, which is bounded on all sides: by the lens, ciliary body, suspensory ligaments and by the retina. It lets light through without refraction, helps maintain the shape of the eye and suspends the delicate lens.

FIG. 1 depicts eye 10 having sclera 12, iris 14, pupil 16, and eyelid 18. FIG. 2 depicts a perspective view of eye 10 with a partial cross-section that depicts lens 20, inferior oblique muscle 22, inferior rectus muscle 24, and optic nerve 26. FIG. 3 is a cross-section of eye 10 and depicts cornea 22 that is optically clear and allows light to pass iris 14 and penetrate lens 20. Anterior chamber 24 underlies cornea 22 and posterior chamber 26 lies between iris 14 and lens 20. Ciliary body 28 is connected to lens 20. FIG. 3 depicts a portion of the conjunctiva 30, which overlies the sclera 12. The vitreous body 32 comprises the jelly-like vitreous humor, with hyaloid canal 34 being in the same. Fovea 36 is in the macula and retina 38 overlies choroid 37. Zonular spaces 42 are depicted.

Figure 4:
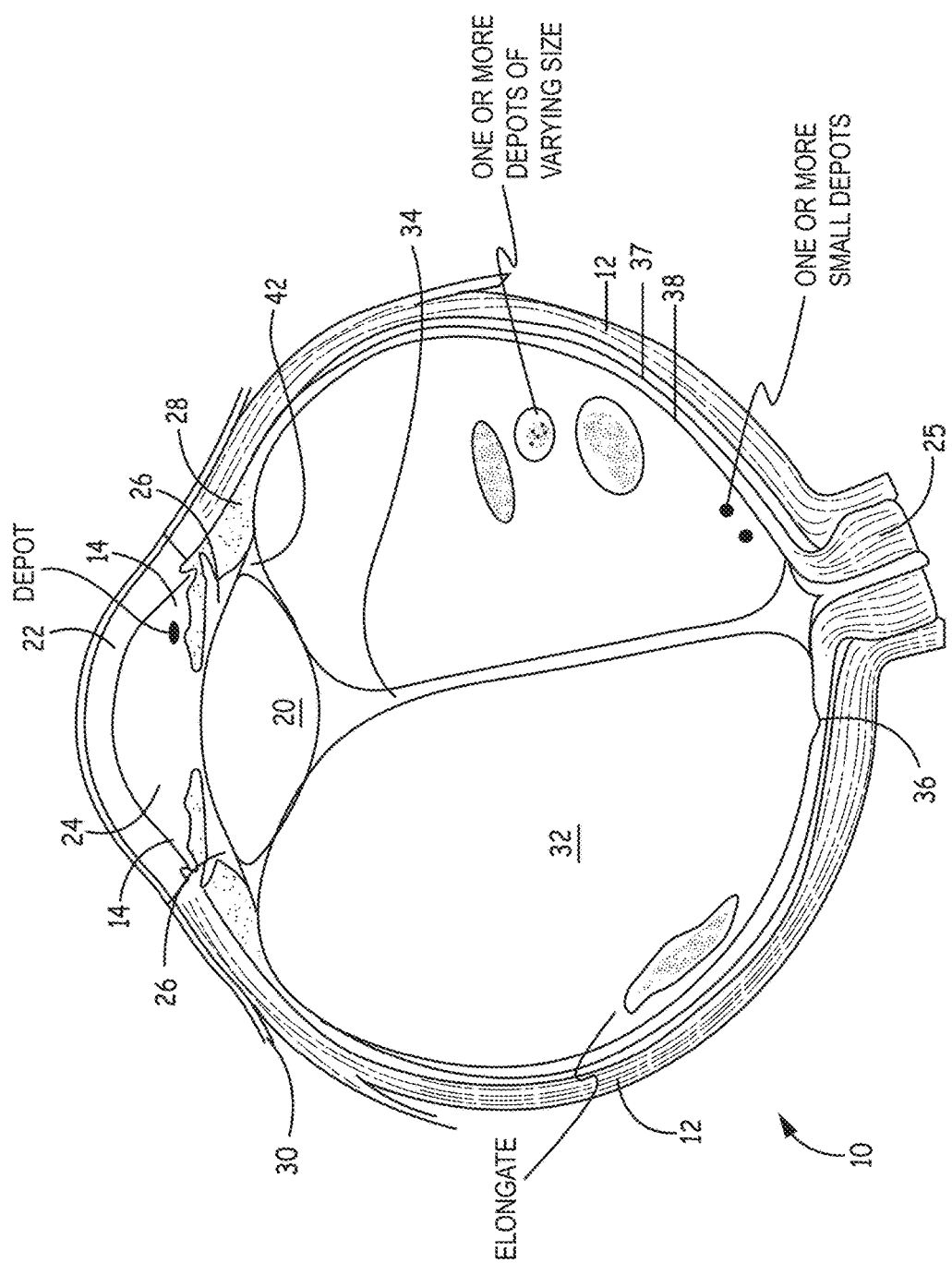
FIG. 4 depicts various delivery alternatives for ocular implants.
Figure 5:
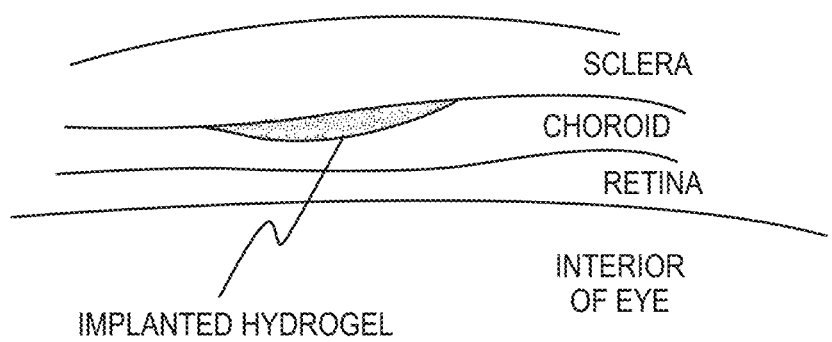
FIG. 5 depicts suprachoroidal material placement.
Figure 6:
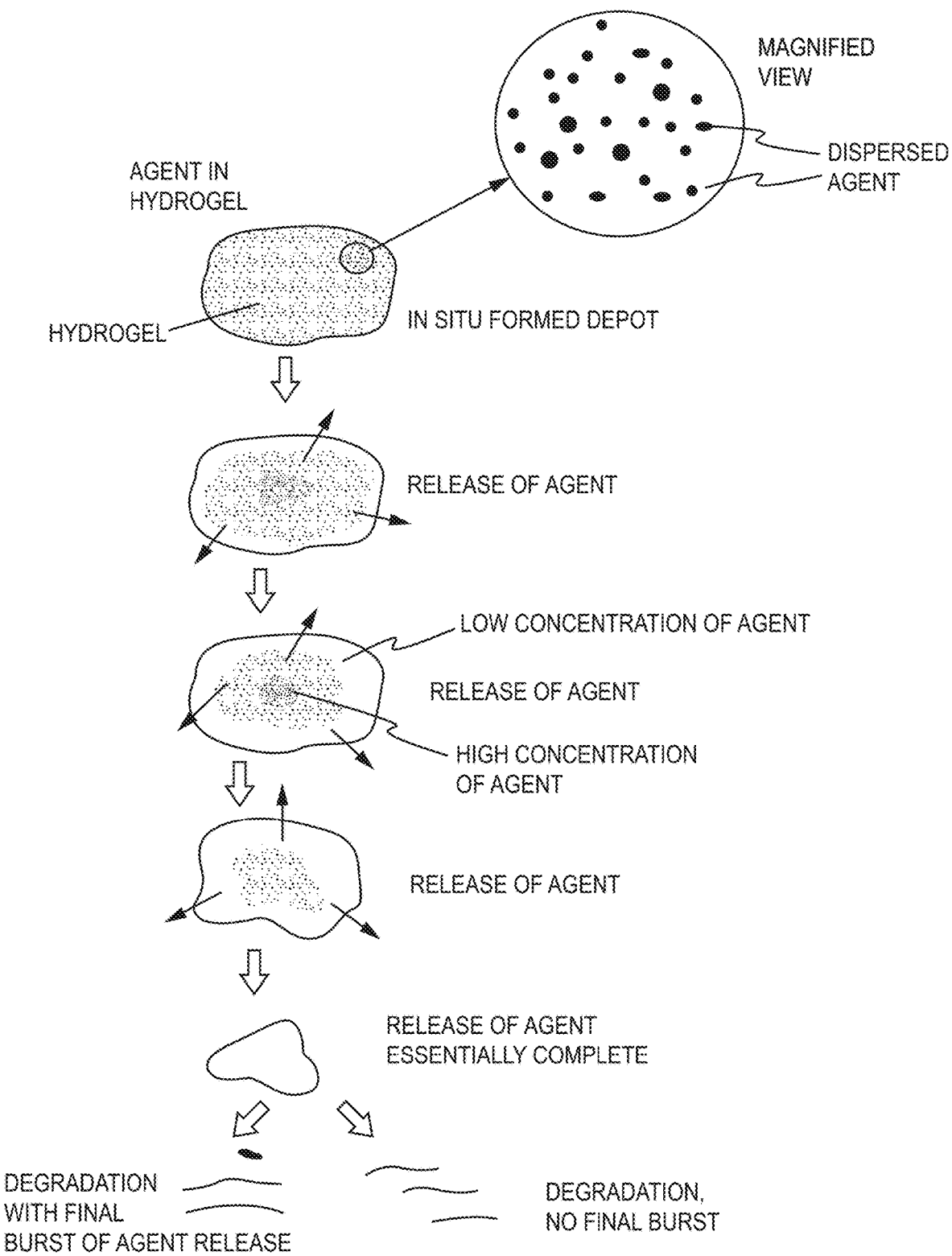
FIG. 6 depicts release of an agent from an in situ formed hydrogel in an intracameral or intravitreal space.

FIG. 4 depicts various intravitreal deposition schemes. A plurality of depots may be formed, or one. The depots may have various shapes, e.g., elongate, spheroidal, spherical, essentially spherical, ellipsoidal, cylindroid, essentially cylindroid, discoidal, or essentially discoidal. The term essentially spherical means that the hydrogel occupies at least 70% of the volume of a sphere drawn around the hydrogel. The term spherical means that the hydrogel occupies at least 85% of the volume of a sphere drawn around the hydrogel. The term essentially discoidal means that the hydrogel occupies at least 70% of the volume of a cylinder drawn around the hydrogel, with a height of the cylinder being less or equal to the diameter of the cylinder. The term essentially discoidal means that the hydrogel occupies at least 85% of the volume of a cylinder drawn around the hydrogel, with a height of the cylinder being less than the diameter of the cylinder. The term essentially cylindroid means that the hydrogel occupies at least 70% of the volume of a cylinder drawn around the hydrogel, with a height of the cylinder being greater than the diameter of the cylinder. The term essentially cylindroid means that the hydrogel occupies at least 85% of the volume of a cylinder drawn around the hydrogel, with a height of the cylinder being greater than the diameter of the cylinder. Other shapes and sizes may be chosen as suited for the site and application, and irregular shapes are also contemplated. Volumes set forth elsewhere herein may be applicable, e.g., less than 1 ml, from 0.005 to 5 ml; Artisans will immediately appreciate that all ranges and values between the explicitly stated bounds are contemplated, with any of the following being available as an upper or lower limit: 10, 20, 25, 50, 100, 150, 200, 250 µL; 0.3, 0.4, 0.5, 0.6, 0.7, 0.8, 0.9, 1.0, 2, 3, 4, 5 mls. One or more such depots may be formed. FIG. 5 illustrates suprachoroidal placement. Other organs may be a site for placement of a hydrogel, as described in more detail below. For instance, the hydrogels may be formed in natural or surgical voids or potential spaces, including other sites where cancer has been removed or is located. Sites include placement of the hydrogel material at a site of a cancer, for example, at a prostate for therapy of prostate cancer or breast cancer.

Application of Precursors to Form Hydrogels In Situ

Back of the eye diseases can be treated with drugs utilizing, e.g., topical, systemic, intraocular and subconjunctival delivery routes. Systemic and topical drug delivery modalities can fall short in delivering therapeutic drug levels to treat posterior segment diseases. These methods of drug delivery encounter diffusion and drug dilution issues due to the inherent anatomical barriers of the intraocular and systemic systems, causing significant patient side effects (due to multiple daily dosing), poor bioavailability and compliance issues. The delivery site for placement of an intraocular drug delivery implant is generally dependent upon the disease that needs to be treated and the type of drug therapy.

The delivery of therapeutic amounts of a drug to the retina in posterior segment eye diseases remains a challenge. Although intravitreal injections into the vitreous cavity of anti-VEGF agents have shown promise to arrest and in some cases reverse chronic age-related diseases like macular degeneration, these techniques and procedures are not without risks and side effects. Intravitreal administration of therapeutic agents into the vitreous cavity can cause cataracts, endophthalmitis and retinal detachments. This form of therapy requires many patients to receive monthly intraocular injections of an anti-VEGF drug over a 12 month time period thus increasing the risk of infection, vitreous wicks and retinal detachments. Embodiments directed to an in situ hydrogel biodegradable drug implant provide an effective alternative treatment for eye diseases, and are expected to reduce the common side-effects associated with repeated intravitreal injections. Embodiments of an intravitreal, intracameral or other ocular biodegradable drug delivery implant system are summarized below.

FIGS. 4 and 5 show certain points of delivery at or near eye 10. Locations include intracamerally, intravitreally or at or near the retina. Hydrogels can be put on the retina although some separation from the retina is typically useful. Separation may be, e.g., 0.1 to 10 mm; Artisans will immediately appreciate that all ranges and values between the explicitly stated bounds are contemplated, with any of the following being available as an upper or lower limit: 0.2, 0.5, 1, 2, 3, 4, 5, 6, 7, 8, 9, 10.

As described in more detail in other sections, a drug depot of the in situ hydrogel drug delivery implant may be designed for controlled, long term drug release ranging from, e.g., about one to about twelve or thirty six months; and may optionally be directed to treatment of diseases of the posterior segment including, for example, age-related macular degeneration, diabetic retinopathy, diabetic macular edema, retinal vein occlusion, and cystoid macular edema. The device can carry a drug payload of various types of therapeutic agents for various conditions.

One mode of application is to apply a mixture of precursors and other materials (e.g., therapeutic agent, viscosifying agent, accelerator, initiator) through a needle, cannula, catheter, or hollow wire to a site in or near an eye. The mixture may be delivered, for instance, using a manually controlled syringe or mechanically controlled syringe, e.g., a syringe pump. Alternatively, a dual syringe or multiple-barreled syringe or multi-lumen system may be used to mix the precursors at or near the site. Syringe-to-syringe mixing may be used when appropriate. Sites where drug delivery depots may be formed include an eye, the anterior chamber, the vitreous, episcleral, in the posterior subtenon's space (Inferior fornix), subconjunctival, sub-tenon, retinal, subretinal, intracanalicular, intracameral, intravitreal, intrascleral, choroidal, suprachoroidal, a retina, subretinal, or a lens, a surface of the cornea or the conjunctiva, among others. Accordingly, embodiments include providing an effective amount or a calculated effective amount at such a site, e.g., an the effective amount at an eye, the anterior chamber, the vitreous, episcleral, in the posterior subtenon's space (Inferior fornix), subconjunctival, sub-tenon, retinal, subretinal, intracanalicular, intracameral, intravitreal, intrascleral, choroidal, suprachoroidal, a retina, subretinal, or a lens, a surface of the cornea or the conjunctiva.

Sites for formation of a hydrogel depot further include a tissue, lumen, void, potential space, inside an animal (human or otherwise), or on a surface of an animal. The term tissue is broad. Sites include iatrogenic sites, sites where tissue is removed, and surgical sites. Sites include cancer tissue, at or near cancer tissue, dental tissue, gums, periodontal, sinus, brain, intravascular, aneurysm, and site of a pathology.

Viscosifying Agents

Viscosifying agents can be useful for hydrogels formed in or on an eye, with the agent helping the solution cling to its site of deposition, or maintain a cohesive mass, while the hydrogel forms. The choice of the agent must be made in light of the kind of crosslinking that is taking place. Viscosity enhancers may be used in conjunction with precursors. In general, the viscosity enhancers do not react with the precursors to form covalent bonds. While it is appreciated that precursors that are generally free of such bonding may sometimes participate in unwanted side reactions, these have little effect on the hydrogel so that the precursors are "free" of such reactions. For instance, if the precursors react by electrophile-nucleophile reactions, the viscosity enhancers may be free of electrophiles or nucleophiles that can form covalent bonds with functional groups of the precursors, even if there is some low level of unwanted side reactions. Viscosity enhancers are, in general, hydrophilic polymers with a molecular weight of at least 20,000, 100,000 or from about 100,000 to about 2,000,000 Daltons; artisans will immediately appreciate that all values and ranges between these explicitly stated values are described, e.g., at least about 100,000, 200,000, more than 500,000, more than 550,000, 600,000. A concentration of about 5% to about 25% w/w may be used, for instance. PEG (e.g., M.W. 100,000 to 250,000) is useful, for example. Viscosity enhancers may be free of electrophiles and/or nucleophiles. Viscosity enhancers may be fee of one or more functional groups such as hydroxyl, carboxyl, amine, or thiol. Viscosity enhancers may include one or more biodegradable links as described herein for precursors. Viscosity enhancers can be useful to prevent precursors from running-off a tissue site before the precursor's crosslink to form a gel.

Another consideration is whether the agent has to pass through a small diameter syringe or catheter, a property referred to as syringeability. A thixotropic viscosifying agent may be used so that, in motion, it provides little resistance but, when static, forms a thick gel. Hyaluronic Acid (HA) has been found to be a useful thixotropic viscosifying agent. Molecular weights (average w/w) from 100,000 to 2,500,000 have been tested. These results show that a higher MW (e.g., 5000 k) may be also be used. Artisans will immediately appreciate that all ranges and values between the explicitly stated bounds are contemplated, e.g., with any of the following being available as an upper or lower limit: 100 k, 200 k, 300 k, 400 k, 500 k, 600 k, 700 k, 800 k, 900 k, 1000 k, 1500 k, 1800 k, 2000 k, 2250 k, 2500 k, 3000 k, 4000 k, 5000 k. Other thixotropic viscosifying agents include high molecular weight polysaccharides, or hydrophilic polymers, or PEGs. A percentage of 0.3 to 2.5% w/w has been tested, with the optimal percentage depending on the MW tested. In general, a polysaccharide in a range of 0.2 to 5% may be added to the hydrogel/hydrogel precursors, Artisans will immediately appreciate that all ranges and values between the explicitly stated bounds are contemplated, with any of the following being available as an upper or lower limit: 0.2, 0.3, 0.4, 0.5, 0.6, 0.7, 1, 2, 2.5, 3, 3.5, 4, 4.5, 5 w/w percent.

Hydrogel Features and Properties

The hydrogel is, in one embodiment, formed from precursors having functional groups that form crosslinks to crosslink the hydrogels and thereby form the hydrogel. The crosslinks may be covalent and/or physical in nature. The hydrogel delivers drugs to the eye or elsewhere. Some embodiments use highly flowable precursors that gel slowly enough to be forced through a very small bore cannula or needle to essentially cross-link only after injection, but nonetheless gel quickly enough so that they do not migrate back through the track of the incision. The gel degrades in the physiological fluid in or around the eye without causing inflammation by degrading into components that are biocompatible and not acidic. In some embodiments the gel adheres to the tissue.

The hydrogel can be made to persist, or essentially persist, until after it has released its therapeutic agent contents, or until it has essentially released the contents. The hydrogel is preferably made so that the agent can diffuse through the hydrogel. One the one hand, allowing the agent to diffuse out of the gel removes an option for controlling a rate of drug delivery. For that reason, conventional practice with drug delivery from degradable materials is to require the material to degrade so that the drug can be released. In the case of a hydrogel, the distance between crosslinks can be made small enough so that a drug cannot move through the hydrogel until it erodes; it is the bioerosion rate that controls release. Nonetheless, abandoning the bioerosion-based approach can be useful. Accordingly, embodiments of the invention may be made with a hydrogel that allows diffusion of a therapeutic agent through the hydrogel. The matrix may be made with a spacing between crosslinks that allows diffusion.

The term essentially released means, unless otherwise indicated, about 97% w/w$_i$ of the drug is released, meaning the drug in the hydrogel had an initial weight w$_i$ and a weight, w, at the time of measurement. Other endpoints may be chosen, for instance, from 50 to 100 percent; Artisans will immediately appreciate that all ranges and values between the explicitly stated bounds are contemplated, with any of the following being available as an upper or lower limit: 50, 60, 70, 80, 85, 90, 95, 96, 97, 98, 99, 99.5, 99.9, 99.99 percent. The term range, unless, otherwise indicated, means that the numerical value can fall anywhere in the range. The term essentially persist means, unless otherwise indicated, about 97% w/w$_i$ of the dry weight of the hydrogel is retained, meaning hydrogel had an initial dry weight w$_i$ and a dry weight, w, at the time of measurement. Other endpoints may be chosen, for instance, from 50 to 100 percent persistence; Artisans will immediately appreciate that all ranges and values between the explicitly stated bounds are contemplated, with any of the following being available as an upper or lower limit: 50, 60, 70, 80, 85, 90, 95, 96, 97, 98, 99, 99.5, 99.9, 99.99 percent. Persistence is the dry weight of the hydrogel relative to an initial dry weight of the hydrogel; this can be measured directly after washing an explanted hydrogel and accounting for the weight of tissue infiltrates, for instance, by digesting the depot and measuring the content of the hydrogel matrix after removing tissue infiltrates. Further, the ranges/values of persistence/release may be mixed and matched. For example, a hydrogel persistence of 95% when the drug is 99% released. As is evident, all of these percentage values are w/w unless otherwise indicated.

It is also useful to speak of the hydrogel/drug combinations in terms of persistence and release at various points. For instance, it may be desirable to have a certain persistence when the release of the agent is at 50%. Accordingly, besides the persistence/release combinations already indicated, there can be a range of persistence from 0% to 100% and a range of release from 0% to 100%; Artisans will immediately appreciate that all ranges and values between the explicitly stated bounds are contemplated, with any of the following being available as an upper or lower limit: 0, 1, 2, 3, 4, 5, 10, 15, 20, 25, 30, 35, 40, 45, 49.9, 50, 50.1, 55, 65, 70, 75, 80, 85, 90, 95, 100, all being w/w percentages. Drug is a broad term that is used interchangeably herein with the term therapeutic agent.

Stability and mechanical integrity are two further factors involved in controlling hydrogels. Stability, in this context, is stability of shape. At a time of formation, a hydrogel might be stable but then lose stability as it loses mechanical integrity, changing its shape, and becoming deformed, expanding or contracting. One measure of stability is change in volume (volume stability). The hydrogel, once hydrated in situ, will have an initial volume. The volume at 24 hours after placement is a usually good measure of initial volume since the hydrogel has fully equilibrated with local fluids and, for gels that degrade in a time span of two or more weeks, little degradation has taken place. Accordingly, hydrogels can be made with an initial volume of 100% and, if they are fully biodegraded, will eventually achieve a volume of 0%. Another metric for stability is the percentage change in position of the initial shape: an overlay of the shape at a point in time is compared to the initial shape (shape stability). The amount of volume of the initial shape that has not been moved and has not disappeared is calculated, with complete stability being 100% and complete ending of stability being 0%. Stability can be described relative to time, as in days, weeks, or months. And/or stability can be described relative to a release of an agent. When a hydrogel designed to be deployed as a cohesive mass is being used in vivo, the forces acting on the hydrogel will typically not deform it from its initial shape so long as the hydrogel retains its initial mechanical integrity. Therefore stability can be used as a proxy for mechanical integrity in many cases. Essentially stable means more than about 97% by shape or volume measure. Shape or volume stability can be set in light of persistence or release, and thus may be chosen to be a value, for example, from 80 to 100 percent when release is from 0 to 100 percent; Artisans will immediately appreciate that all ranges and values between the explicitly stated bounds are contemplated, with any of the following being available as an upper or lower limit: 0, 1, 2, 3, 4, 5, 10, 15, 20, 25, 30, 35, 40, 45, 49.9, 50, 50.1, 55, 65, 70, 75, 80, 85, 90, 95, 100, all being percentages of shape or volume or w/w release percentages.

Stability and mechanical integrity can also be used to reference an injectable solution that comprises precursor(s) and maintains shape and mechanical integrity within a space from injection until it gels, whether that space be a vitreous body, or other location. Examples of another space are puncta (canaliculus, upper/lower canaliculus), ocular fornix, upper/lower ocular fornix, subtenon space, choroid, suprachoroid, tenon, cornea, cancer tissue, organ, prostate, breast, surgically created space or injury, void space, and potential space. Embodiments include in situ formation of a punctal plug, with precursor(s) being introduced into the canaliculus and forming a punctal plug there. Accordingly, the shape and volume stability, described above, is contemplated for the solution.

In general, precursors may be combined as described herein at a site in or near an eye or other tissue to make a crosslinked hydrogel that comprises a therapeutic agent that is released into the eye to treat a disease over a suitable period of time. The hydrogel may be low-swelling, as measurable by the hydrogel having a weight increasing no more than about 10% or about 50% upon exposure to a physiological solution for twenty-four hours relative to a weight of the hydrogel at the time of formation; artisans will immediately appreciate that all the ranges and values within the explicitly stated ranges are contemplated. The hydrogel also may be water-degradable, as measurable by the hydrogel being dissolvable in vitro in an excess of water by degradation of water-degradable groups in the hydrogel. A composition with the precursors mixed therein can be introduced through a small-gauge needle provided that the composition has a suitable viscosity, which in turn depends on precursor properties, concentrations, and chemistry. Further, the hydrogels' mechanical strengths and reaction time are adjusted though control of the precursors and functional groups. The precursors and hydrogels may have various features that can be mixed-and-matched as guided by the considerations for making an effective device; the following sections describe some of these features.

Precursor Materials

The hydrogels are made from precursors. Precursors are chosen in consideration of the properties that are desired for the resultant hydrogel. There are various suitable precursors for use in making the hydrogels. The term precursor refers to those molecules crosslinked to form the hydrogel matrix. While other materials might be present in the hydrogel, such as therapeutic agents or fillers, they are not precursors. The term matrix is applicable for hydrogels. Such matrices include matrices with a water content of more than about 20% w/w; Artisans will immediately appreciate that all ranges and values between the explicitly stated bounds are contemplated, with any of the following being available as an upper or lower limit: 20%, 99%, 80%, 95%, at least 50%, and so forth, with the percentages being w/w and the solvent being water for hydrogels. Hydrogels may be formed by crosslinking water soluble molecules to form networks of essentially infinite molecular weight. Hydrogels with high water contents are typically soft, pliable materials. Hydrogels and drug delivery systems as described in U.S. Publication Nos. 2009/0017097, 2011/0142936 and 2012/0071865 may be adapted for use with the materials and methods herein by following the guidance provided herein; these references are hereby incorporated herein by reference for all purposes, and in case of conflict, the instant specification is controlling.

Hydrogels may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, and the like, also form hydrogels upon contact with aqueous surroundings.

Hydrogels may be biostable or biodegradable. Examples of biostable hydrophilic polymeric materials are poly(hydroxyalkyl methacrylate), poly(electrolyte complexes), poly (vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-cross-linked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

Hydrogels may be made from precursors. The precursors are crosslinked with each other. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form matrices and/or polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein. Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule. Some precursors react by a step growth mechanism, and are polymers formed by the stepwise reaction between functional groups of monomers. Most step growth polymers are also classified as condensation polymers, but not all step growth polymers release condensates. Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons. The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be covalently crosslinked together. In general, polymeric precursors are polymers that will be joined to other polymeric precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic molecule, e.g., a precursor or precursor portion, has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic. As is customary in these arts, the term PEG is used to refer to PEO with or without hydroxyl end groups.

A precursor may also be a macromolecule (or macromer), which is a molecule having a molecular weight in the range of a thousand to many millions. The hydrogel may be made with at least one of the precursors as a small molecule of about 1000 Da or less (alternatively: 2000 Da or less). The macromolecule, when reacted in combination with a small molecule (of about 1000 Da or less/200 Da or less), is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000. There are certain advantage to having a small molecule, such as diffusivity for completion of reactions.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Embodiments of the invention include choosing a low-solubility agent or agent with other solubility as set forth herein and choosing a precursor that comprises hydrophobic and hydrophilic portions. The hydrophobic/hydrophilic precursor may comprise one or more functional groups: nucleophiles or electrophiles. The hydrophilic portion, the hydrophobic portion, or both, may be chosen to receive such functional groups.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in U.S. Publication Nos. 2004/0086479 and 2004/0131582 and PCT Publication Nos. WO07005249, WO07001926 and WO06031358, or the U.S. counterparts thereof; dendrimers may also be useful as multifunctional precursors, e.g., as in U.S. Publication Nos. 2004/0131582 and 2004/0086479 and PCT Publication Nos. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. Molecular weights expressed herein are number average molecular weights unless otherwise specified. NH2 refers to an amine termination. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable or water-degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels, as well as compositions that comprise the same, may be provided in a form that is pharmaceutically acceptable, meaning that it is highly purified and free of contaminants, e.g., pyrogens.

Hydrogel Structures

The hydrogel's structure and the material composition of the hydrogel's precursors determine its properties. Precursor factors include properties such as biocompatibility, water solubility, hydrophilicity, molecular weight, arm length, number of arms, functional groups, distance between crosslinks, degradability, and the like. The choice of reaction conditions also effects the hydrogel's structure and properties, including choices of solvents, reaction schemes, reactant concentrations, solids content, and the like. There can be a variety of ways to achieve certain properties, or combination of properties. On the other hand some properties are in tension with each other, for instance brittleness may increase as a distance between crosslinks or solids content increases. Strength may be increased by increasing the number of crosslinks but swelling may thereby be reduced. Artisans will appreciate that the same materials may be used to make matrices with a great range of structures that will have highly distinct mechanical properties and performance, such that the achievement of a particular property should not be merely assumed based on the general types of precursors that are involved.

The spacing between molecular strands of the hydrogel (the matrix) affects several hydrogel properties, including a rate of diffusion of molecules. The crosslinking density can be controlled by the choice of the overall molecular weight of the precursor(s) used as crosslinker(s) and other precursor(s) and the number of functional groups available per precursor molecule. A lower molecular weight between crosslinks such as 200 will give much higher crosslinking density as compared to a higher molecular weight between crosslinks such as 500,000; artisans will immediately appreciate that all ranges and values within this range are contemplated and supported, e.g., 200 to 250,000, 500 to 400,000, 5,000, 10,000, 20,000, 30,000, 40,000, 50,000, 60,000, 70,000, 80,000, 90,000, 100,000, and so forth. The crosslinking density also may be controlled by the overall percent solids of the crosslinker and functional polymer solutions. Yet another method to control crosslink density is by adjusting the stoichiometry of nucleophilic functional groups to electrophilic functional groups. A one to one ratio leads to the highest crosslink density. Precursors with longer distances between crosslinkable sites form gels that are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 2,000 to 100,000; artisans will immediately appreciate that all the ranges and values within the explicitly stated ranges are contemplated, e.g. 5,000 to 35,000. The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%. One way to construct the materials so that the delay is controlled or minimized is to design the hydrogels with different rates of diffusion for the agent. Often the molecular weight (MW) of the agent is the controlling variable. There are a number of approaches for relating hydrogel properties to diffusion. These include the free volume theory, the hydrodynamic theory, the obstruction theory, combination theories, and parameters such as mesh size, sieving terms, distributions of openings between chains, and so forth (Amsden, Macromolecules (1998) 31:8382-8395). In practice, however, hydrogels can be made with various distances between their crosslinks and tested for a particular molecule to create a hydrogel that provides a desired diffusion rate. In general, a distance between crosslinks that is large compared to the molecule's size provides for a high rate of diffusion, a distance between crosslinks that is small compared to the molecule's size provides for a slow diffusion, and a distance between crosslinks that is smaller than the molecule provides for essentially no diffusion. A molecule's molecular weight is generally a useful measure of it size. There are other factors that can be important and these can be accounted for when creating the hydrogel: for instance, interactions between the molecule and the hydrogel, such as affinity or charge-charge, and solvent effects such as hydrophobicity of the molecule.

Reaction kinetics are generally controlled in light of the particular functional groups unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction, so that some embodiments have at least one precursor with a molecular weight of at least 5,000 to 50,000 or 150,000 Daltons. Preferably the crosslinking reaction leading to gelation occurs within about 0.1 to about 10 or to about 30 minutes; artisans will immediately appreciate that all the ranges and values within the explicitly stated ranges are contemplated, e.g., at least 120 seconds, or between 5 to 600 seconds, e.g., 5, 10, 30, 60, 100, 200, 300 seconds. Gelation time is measured by applying the precursors to a flat surface and determining the time at which there is substantially no flow down the surface when it is titled at an angle of about 60 degrees (i.e., a steep angle, close to perpendicular).

The hydrogel is generally low-swelling, as measurable by the hydrogel having a weight increasing no more than about 0% to about 10% or to about 50% upon exposure to a physiological solution for twenty-four hours relative to a weight of the hydrogel at the time of formation. One embodiment for reducing swelling is to increase the number of crosslinks, bearing in mind, however, that crosslinks can increase rigidity or brittleness. Another embodiment is to reduce the average chain distance between crosslinks. Another embodiment is to use precursors with many arms, as explained below.

Another embodiment to reduce swelling is to control the degree of hydrophilicity, with less hydrophilic materials tending to swell less; for instance, highly hydrophilic materials such as PEOs can be combined with less hydrophilic materials such as PPO or even hydrophobic groups such as alkyls.

Another embodiment to reduce swelling is to choose precursors that have a high degree of solvation at the time of crosslinking but subsequently become less solvated and having a radius of solvation that effectively shrinks; in other words, the precursor is spread-out in solution when crosslinked but later contracts. Changes to pH, temperature, solids concentration, and solvent environment can cause such changes; moreover, an increase in the number of branches (with other factors being held effectively constant) will tend to also have this effect. The number of arms are believed to sterically hinder each other so that they spread-out before crosslinking, but these steric effects are offset by other factors after polymerization. In some embodiments, precursors have a plurality of similar charges so as to achieve these effects, e.g., a plurality of functional groups having a negative charge, or a plurality of arms each having a positive charge, or each arm having a functional group of similar charges before crosslinking or other reaction.

Hydrogels described herein can include hydrogels that swell minimally after deposition. Such medical low-swellable hydrogels may have a weight upon polymerization that increases no more than, e.g., about 50%, about 10%, about 5%, about 0% by weight upon reaching an equilibrium water content upon exposure to a physiological solution, or that shrink (decrease in weight and volume), e.g., by at least about 5%, at least about 10%, or more. Artisans will immediately appreciate that all ranges and values within or otherwise relating to these explicitly articulated limits are disclosed herein. Unless otherwise indicated, swelling of a hydrogel relates to its change in volume (or weight) between the time of its formation when crosslinking is effectively complete and the time after being placed in vitro a physiological solution in an unconstrained state for twenty-four hours, at which point it may be reasonably assumed to have achieved its equilibrium swelling state. For most embodiments, crosslinking is effectively complete within no more than about fifteen minutes such that the initial weight can generally be noted at about 15 minutes after formation as Weight at initial formation. Accordingly, this formula is used: % swelling=[(Weight at 24 hours−Weight at initial formation)/Weight at initial formation]*100. n the case of hydrogels that have substantial degradation over twenty-four hours, the maximum weight may be used instead of a 24-hour weight, e.g., as measured by taking successive measurements. The weight of the hydrogel includes the weight of the solution in the hydrogel. A hydrogel formed in a location wherein it is constrained is not necessarily a low-swelling hydrogel. For instance, a swellable hydrogel created in a body may be constrained from swelling by its surroundings but nonetheless may be a highly swellable hydrogel as evidenced by measurements of its swelling when unconstrained and/or the forces against a constraint.

Functional Groups

The precursors for covalent crosslinking have functional groups that react with each other to form the material via covalent bonds, either outside a patient, or in situ. The functional groups generally are polymerizable, a broad category that encompasses free radical, addition, and condensation polymerization and also groups for electrophile-nucleophile reactions. Various aspects of polymerization reactions are discussed in the precursors section herein.

Thus in some embodiments, precursors have a polymerizable group that is activated by photoinitiation or redox systems as used in the polymerization arts, or electrophilic functional groups, for instance: carbodiimidazole, sulfonyl chloride, chlorocarbonates, n-hydroxysuccinimidyl ester, succinimidyl ester or sulfasuccinimidyl esters, or as in U.S. Pat. No. 5,410,016 or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfo-succinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

One embodiment has reactive precursor species with 2 to 16 nucleophilic functional groups each and reactive precursor species with 2 to 16 electrophilic functional groups each; artisans will immediately appreciate that all the ranges and values within the explicitly stated ranges are contemplated, for instance 2, 3, 4, 5, 6, 7, 8, 9, 10, 11, 12, 13, 14, 15, or 16 groups.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2, 2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Precursors for making hydrogels and/or hydrogels made from precursors may be free of one or more of: initiators, photoactivable groups, and visualization agents, imaging agents.

Visualization Agents

A visualization agent may be present in the hydrogel; it reflects or emits light at a wavelength detectable to a human eye so that a user applying the hydrogel could observe the object when it contains an effective amount of the agent. Chemicals that require a machine aid for imaging are referred to as imaging agents herein, and examples include: radioopaque contrast agents and ultrasound contrast agents. Some biocompatible visualization agents are FD&C BLUE #1, FD&C BLUE #2, and methylene blue. These agents, if used, are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the xerogel/hydrogel, thus preserving visualization after application to a patient until the hydrogel hydrolyzes to dissolution. Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive imaging agents such as NHS-fluorescein can be incorporated into the molecular network of the xerogel/hydrogel. Fluorescein is typically an imaging agent unless indicated as being in sufficient concentrations to be visualized without machine aid. The visualization agent may be present with either reactive precursor species, e.g., a crosslinker or functional polymer solution. The preferred colored substance may or may not become chemically bound to the hydrogel.

Biodegradation

An hydrogel may be formed so that, upon hydration in physiological solution, a hydrogel is formed that is water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, and/or free of precursors that degrade into acid or diacids, and/or free of PLA, PLGA, PLA/PLGA.

For example, electrophilic groups such as SG (N-hydroxysuccinimidyl glutarate), SS (N-hydroxysuccinimidyl succinate), SC (N-hydroxysuccinimidyl carbonate), SAP (N-hydroxysuccinimidyl adipate) or SAZ (N-hydroxysuccinimidyl azelate) may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate <polylactate <polytrimethylene carbonate <polycaprolactone. Thus it is possible to construct a hydrogel with a desired degradation profile, from a few days to many months, using a degradable segment. Some embodiments include precursors that are free of adjacent ester groups and/or have no more than one ester group per arm on one or more of the precursors: control of the number and position of the esters can assist in uniform degradation of the hydrogel.

A biodegradable linkage in the organogel and/or xerogel and/or hydrogel and/or precursor may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages (or just one biodegradable linkage, for example an ester) present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

The eye is a very sensitive organ. The inventors observed that fragmentation of biodegradable implants in the eye was a particular factor that was contradicting biocompatibility. Besides its sensitivity, the interior of the eye is a small space such that the agent has to be present at a high concentrations if an extended time of release is a goal. It is believed, without being bound to a single theory, that, in this environment in particular, the presence of the drug when implants reached a stage of becoming fragmented is exacerbating bio-responses to the materials. The macrophages can begin to recognize the drug as a foreign substance when the fragments are cell-sized or bacterial-sized. Biologic drugs tend to provoke this response, but even small molecule drugs are believed to have an unwanted enhancing effect. Therefore, instead of minimizing persistence of the implant, embodiments include hydrogels with an extended persistence time that enhances biocompatibility. The persistence time may be extended until the agent, or agents, in the hydrogel are fully released. This approach enhances biocompatibility.

Drugs or Other Therapeutic Agents for Delivery

Therapeutic agents include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PAL- LADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (aflibercept or VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™) sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of BIBW 2992 (small molecule targeting EGFR/Erb2), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (small molecule commercially available from Esai, Co.)

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antibiotics, pain relievers, inhibitors of vascular endothelial growth factor (VEGF), chemotherapeutics, antiviral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. Examples of steroids are flunisolide (solubility 90 µg/mL), betamethasone sodium phosphate (freely soluble in water), budesonide (30 µg/mL, and triamcinolone acetonide (20 µg/mL). The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides and proteins. The term protein, as used herein, refers to peptides of at least about 5000 Daltons. The term peptide, as used herein, refers to peptides of any size. The term oligopeptide refers to peptides having a mass of up to about 5000 Daltons. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, contains bevacizumab, which is an antibody that binds VEGF. And AFLIBERCEPT is a fusion protein that includes portions of a VEGF receptor to trap VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. Fovista is a pegylated anti-PDGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Oxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, permeation agents for an eye.

Solubilities of Therapeutic Agents

Embodiments of the invention include a method of drug delivery to a tissue, eye, intracameral space, or other sites set forth herein comprising forming a hydrogel in situ with a drug in the hydrogel (e.g., dissolved, suspended, liquid, solid, or dispersed throughout), the drug having a low solubility in water or other solubility as set forth herein. Examples of such agents are, in general, TKIs. Low-solubility is a broad term that means no more than 200 µg/ml soluble in water at 25° C., the water being pure water, and the drug being essentially pure or a salt. Similarly, very low solubility is a broad term that means no more than 50 µg/ml soluble in water at 25° C. Other descriptive terms are set forth in Table 1 and have the definition provided therein, and are directed to bands of solubility, except for practically insoluble or insoluble, which is a defined as having an upper limit. Artisans will immediately appreciate that all ranges and values between the explicitly stated bounds are contemplated, with any of the following solubilities being available as an upper or lower limit: 200,000, 100,000, 33,000, 10,000, 1,000, 225, 200, 150, 100, 50, 25, 20, 1, e.g., less than 100 or less than 50, or less than 20 µg/ml soluble in water, or from 0.001 to 225, 1 to 200, 2 to 125 µg/ml soluble in water.

The United States Pharmacopeia defines relative solubility in descriptive terms of various compendial substances, and these descriptive terms can be translated into quantitative solubility using the units of micrograms per milliliter, as shown in Table 1. Various forms of pharmacological agents are suitable for sustained release from in situ formed hydrogel depots. Suitable drugs would include various agents, e.g. as set forth herein, antibacterials, antifungals, antivirals, anti-angiogenesis, anti-allergy, steroids, immunosuppressants, glaucoma drugs, NSAIDs, and so forth, of both small and large (where applicable) molecular size.

The sustained release of small molecules from the depot can be controlled by their limited solubility and agents classified as very slightly soluble, practically insoluble, or insoluble would be generally preferable candidates as exemplified in the Table 2. Experimental water solubility (when available in the scientific literature) is added into the table to support the descriptive term. This experimental aqueous and/or water solubility is often dependent upon test conditions (pH, temperature) and it is understood that variation in these conditions may alter the experimental solubility value. It should be understood that solubility is controlled by many factors, of particular interest is the difference in solubility of various salts forms of the same parent drug molecule. For instance a dexamethasone sodium phosphate salt form is considered soluble whereas either a dexamethasone alcohol or acetate is considered practically insoluble, or insoluble, as shown in Table 2.

It should be understood that all drugs can also be released from the hydrogel depot using a secondary forms of encapsulation to potentially provide a more tailored drug release profile which is not regulated by drug solubility, but rather by degradation of the microparticles. For examples, drugs classified as slightly soluble to very soluble most likely require a secondary form of encapsulation (e.g. microparticles) to provide sustained release.

Because the hydrogel is formed during crosslinking of PEG arms it forms a network structure with a defined porosity of limited molecular size. The entrapment of large macromolecules, such as anti-angiogenesis biologics shown in Table 2, which exceed that limited molecular size are therefore physically entrapped within the hydrogel network. Therefore degradation of the gel network is necessary to release the entrapped large macromolecules even though these macromolecules would be considered to be soluble to very soluble.

TABLE 1

USP Descriptive Solubility

| Descriptive Term | Parts of Solvent Required for 1 Part of Solute | Solubility Range (µg/mL) |
| --- | --- | --- |
| Very soluble | Less than 1 | >1,000,000 |
| Freely soluble | From 1 to 10 | 100,000-1,000,000 |
| Soluble | From 10 to 30 | 33,000-100,000 |
| Sparingly soluble | From 30 to 100 | 10,000-33,000 |
| Slightly soluble | From 100 to 1000 | 1,000-10,000 |
| Very slightly soluble | From 1000 to 10,000 | 100-1,000 |
| Practically insoluble, or Insoluble | 10,000 and over | <100 |

TABLE 2

Descriptive Solubility of Agents for Potential Sustained Release from In Situ Formed Hydrogel Depots

| Class | Agent | Descriptive Solubility | Experimental Solubility |
| --- | --- | --- | --- |
| Anti-angiogenesis - small molecules | Axitinib | Practically Insoluble | 1 µg/mL |
| | Cabozantinib (XL184, BMS-907351) | Practically Insoluble | — |
| | Cediranib (AZD2171) | Sparingly Soluble | — |
| | Dovitinib (TKI-258) Dilactic Acid | Soluble | — |
| | Imatinib Mesylate (STI571) | Very Soluble | — |
| | Lenvatinib (E7080) | Practically Insoluble | — |
| | Linifanib (ABT-869) | Practically Insoluble | — |
| | Masitinib (AB1010) | Practically Insoluble | — |
| | Motesanib Diphosphate (AMG-706) | Sparingly Soluble | — |
| | Nilotinib Hydrochloride | Practically Insoluble | — |
| | Nintedanib (BIBF 1120) | Practically Insoluble | — |
| | OSI-930 | Practically Insoluble | — |
| | Pazopanib | Practically Insoluble | — |
| | Pazopanib HCl (GW786034 HCl) | Practically Insoluble | — |
| | Regorafenib (BAY 73-4506) | Practically Insoluble | — |
| | Semaxanib (SU5416) | Practically Insoluble | — |
| | Sorafenib Tosylate | Practically Insoluble | — |
| | Sunitinib Malate | Soluble | 25,000 µg/mL |
| | Telatinib | Practically Insoluble | — |
| | Tivozanib (AV-951) | Practically Insoluble | — |
| | TSU-68 (SU6668, Orantinib) | Practically Insoluble | — |
| | Vandetanib (ZD6474) | Practically Insoluble | 8 µg/mL |
| | Vatalanib (PTK787) 2HCl | Sparingly Soluble | — |
| Anti-Angiogenesis - Biologic | Bevacizumab | Soluble | >33,000 µg/mL |
| | Ranibizumab | Soluble | >33,000 µg/mL |
| | Aflibercept | Freely Soluble | >100,000 µg/mL |
| Immuno-suppressants | Cyclosporine A | Practically Insoluble | 28 µg/mL |
| | Everolimus | Practically Insoluble | 10 µg/mL |

TABLE 2-continued

Descriptive Solubility of Agents for Potential Sustained Release from In Situ Formed Hydrogel Depots

| Class | Agent | Descriptive Solubility | Experimental Solubility |
|---|---|---|---|
| | Tacrolimus | Practically Insoluble | 8 μg/mL |
| | Sirolimus | Practically Insoluble | <100 μg/mL |
| | Pimecrolimus | Practically Insoluble | — |
| Steroids | Beclomethasone Dipropionate | Practically Insoluble | 49 mg/L |
| | Betamethasone Sodium Phosphate | Practically Insoluble | 67 μg/mL |
| | Budesonide, Micronized | Practically Insoluble | 20 μg/mL |
| | Flunisolide, Anhydrous, USP | Practically Insoluble | 90 μg/mL |
| | Fluticasone Propionate | Practically Insoluble | 1 μg/mL |
| | Triamcinolone Acetonide | Practically Insoluble | 80 mg/L |
| | Triamcinolone Hexacetonide | Practically Insoluble | 4 μg/mL |
| | Triamcinolone Diacetate | Practically Insoluble | 35 μg/mL |
| | Dexamethasone alcohol | Practically Insoluble | 89 μg/mL |
| | Dexamethasone acetate | Practically Insoluble | 6 μg/mL |
| | Dexamethasone sodium phosphate | Soluble | 50,0000 μg/mL |
| | Prednisolone | Very slightly soluble | 223 μg/mL |
| | Methylprednisolone | Very slightly soluble | 120 μg/mL |
| | Prednisolone acetate | Practically Insoluble | 17 μg/mL |
| | Loteprednol etabonate | Practically Insoluble | 5 μg/mL |
| | Difluprednate | Practically Insoluble | — |
| | Fluorometholone | Practically Insoluble | 30 μg/mL |
| | Flurbiprofen Sodium | Practically Insoluble | 61 μg/mL |
| | Fluocinolone Acetonide | Practically Insoluble | — |
| | Triamcinolone Acetonide | Practically Insoluble | 18 μg/mL |
| | Triamcinolone Hexacetonide | Practically Insoluble | 4 μg/mL |
| | Mometasone furoate | Practically Insoluble | 20 μg/mL |
| | Budesonide | Practically Insoluble | 24 μg/mL |
| NSAIDs | Ibuprofen | Practically Insoluble | 21 μg/mL |
| | Meclofenamate sodium | Freely Soluble | — |
| | Mefanamic Acid | Practically Insoluble | — |
| | Naproxen Sodium | Soluble | — |
| | Flurbiprofen | Practically Insoluble | — |
| | Fenoprofen Calcium | Slightly Soluble | — |
| | Celecoxib | Slightly Soluble | 3,300 μg/mL |
| | Nepafenac | Practically Insoluble | 14 μg/mL |
| | Bromfenac | Soluble | 53,000 μg/mL |
| | Ketorolac Tromethamine | Freely Soluble | — |
| | Diclofenac | Very Slightly Soluble | 600 μg/mL |
| Antibiotics | Moxifloxacin HCl | Sparingly Soluble | — |
| | Besifloxacin Base | Practically Insoluble | 90 μg/mL |
| | Besifloxacin HCl | Sparingly Soluble | |

TABLE 2-continued

Descriptive Solubility of Agents for Potential Sustained Release from In Situ Formed Hydrogel Depots

| Class | Agent | Descriptive Solubility | Experimental Solubility |
|---|---|---|---|
| | Ciprofloxacin HCl | Sparingly Soluble | — |
| | Ofloxacin | Sparingly Soluble | 28,000 µg/mL |
| | Gatifloxacin | Soluble | 60,000 µg/mL |
| | Azithromycin | Practically Insoluble | 69 µg/mL |
| Anti-Virals | Trifluridine | Slightly Soluble | 1,500 µg/mL |
| | Ganciclovir | Slightly Soluble | 4,300 µg/mL |
| Glaucoma Drugs | Travoprost | Practically Insoluble | 44 µg/mL |
| | Latanoprost | Practically Insoluble | 40 µg/mL |
| | Bimatoprost | Slightly Soluble | — |
| | Timolol Maleate | Soluble | 2,800 µg/mL |
| | Tafluprost | Practically Insoluble | — |
| Antihistamine - Mast Cell Stabilizer | Ketotifen base | Practically Insoluble | 15 µg/mL |
| | Ketotifen fumarate | Slightly Soluble | 10,000 µg/mL |
| | Azelastine Base | Practically Insoluble | 50 µg/mL |
| | Azelastine Embonate | Practically Insoluble | 15 µg/mL |
| | Olopatadine HCl | Slightly Soluble | 2,0000 µg/mL |

Eye Disease States

The materials described herein may be used to deliver drugs or other therapeutic agents (e.g., imaging agents or markers) to eyes or tissues nearby. Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Disease is a broad term that generally includes pathologies. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other conditions are further discussed elsewhere herein.

Hydro Gel Loading with Agents; Preparation as Particles

The hydrogels may be loaded with an agent or agents that are disposed directly and/or indirectly in the hydrogel. While encapsulation in particles is not preferred in some circumstances, it can be useful to place agents into particles, especially outside the eye. Encapsulation may involve mixing an agent with a biodegradable material. Directly refers to placing the agent in direct contact with the matrix, e.g., by forming a matrix in a presence of the agent in solid or soluble form. An indirect loading process is, e.g., placing the agent in particles and forming the hydrogel around them, so that the agent is inside the particle and, at the time of formation, is not in direct contact with the matrix. Biodegradable vehicles in which the active agent may be present include: encapsulation vehicles, such as microparticles, microspheres, microbeads, micropellets, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly (glycolic acid)-co-poly(glycolic acid), poly (orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone)s and poly (hydroxy acid) are useful as biodegradable encapsulation vehicles. The therapeutic agent or encapsulated therapeutic agent may be present in solution or suspended form. Further, a particle may be made that is free of one or more of: binders, non-peptidic polymers, surfactants, oils, fats, waxes, hydrophobic polymers, polymers comprising alkyl chains longer than 4 $CH_2$ groups, phospholipids, micelle-forming polymers, micelle-forming compositions, amphiphiles, polysaccharides, polysaccharides of three or more sugars, fatty acids, and lipids. Lyophilized, spray dried or otherwise processed proteins are often formulated with sugars such as trehalose to stabilize the protein through the lyophilization or other processes used to prepare the proteins. These sugars may be allowed to persist in the particle throughout the organogel/xerogel process. The particles may be made to comprise between about 10% and about 100% (dry w/w) protein; artisans will immediately appreciate that all the ranges and values within the explicitly stated ranges are contemplated, e.g., about 40% to about 80% or at least 50% or at least 80% or at least 90% or at least 99%.

A gel or organogel or hydrogel may be formed around an agent and then reduced to encapsulating particles that are subsequently treated to remove the organic or aqueous solvent or solvents to form a xerogel particle. For an injectable form, the organogel or hydrogel can be macerated, homogenized, extruded, screened, chopped, diced, or otherwise reduced to a particulate form. Alternatively, the organogel or hydrogel can be formed as a droplet or a molded article containing the suspended protein particles.

One process for making such particles involves creation of a material that is broken up to make the particles.

The particles may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated, e.g., from about 1 to about 10 µm or from about 1 to about 30 µm. About 1 to about 500 microns is another such range that is useful, with sizes falling throughout the range and having a mean sizing at one value within the range, and a standard deviation centered around the mean value, e.g., from about 1% to about 100%. A simple method for sizing particles involves using custom-made or standardized sieve mesh sizes. The term particle is broad and includes spherical, cylindrical, discoidal, and irregularly shaped particles. Embodiments include making a plurality of collections of particles, with the collections having different rates of degradation in vivo, and mixing collections for a degradation performance as desired.

Kits or Systems

Kits or systems for making hydrogels may be prepared. The kits are manufactured using medically acceptable conditions and contain precursors that have sterility, purity and preparation that is pharmaceutically acceptable. The kit may contain an applicator as appropriate, as well as instructions. A therapeutic agent may be included pre-mixed or available for mixing. Solvents/solutions may be provided in the kit or separately, or the components may be pre-mixed with the solvent. The kit may include syringes and/or needles for mixing and/or delivery. In some embodiments, the kit has at least one precursor and an applicator. Visualization or imaging agents may be incorporated into the material. The kit may include a viscosifying agent, e.g., a hyaluronic acid, pre-mixed or separate from other components. Embodiments include kits comprising one or more precursors set forth herein and one or more agents set forth herein, optionally with an applicator and solvent (e.g., water) for making solutions of precursors and/or agents.

One or more of the precursors may be provided in dry form (e.g., cake, powder, immobilized pellet). A diluent for the same may be included, e.g., aqueous. A buffer may be in the dry material, the diluent, or both. A process for making a dry precursor is, for instance, making the precursor in, or dissolving it in, an organic solution. If the functional groups are electrophiles, the solvent and/or pH may be chosen so that the electrophiles are unreactive. If the precursor comprises hydrolytically labile groups, such as many forms of esters, the solvent may be chosen to be free of water, e.g., a dry organic solvent, dimethyl carbonate (DMC), dimethylformamide (DMF), polar aprotic solvents. The precursor solution may be frozen and lyophilized. The lyophilate can be ground or otherwise reduced to a powder, compressed to a cake, made into a pellet, or lyophilized in its end-use container.

In some embodiments, kits having precursors and other materials as needed to form a hydrogel in situ with a therapeutic agent may be provided, with the component parts including those described herein. In some embodiments, features of the hydrogels can thus be chosen to make hydrogels that are minimally swelling, delivered through a small needle, can be put into an aqueous low viscosity preparation to gel after placement. The use of fluent aqueous precursors to form a biodegradable drug depot allows for administration through small (e.g., 30 gauge) needles. Also, since the hydrogel can be made to not break down into acidic byproducts, the drug depots are well tolerated by sensitive tissues, such as the eye.

Due to this, the implants can be made rather large in size (e.g., 1 ml capacity, referring to the eye) relative to implants that are made from conventional biodegradable polymers, which are conventionally much smaller. On the other hand, small depots can also be useful. Accordingly, some embodiments are hydrogels with volumes between about 0.005 to about 5 ml; artisans will immediately appreciate that all the ranges and values within the explicitly stated ranges are contemplated, e.g., 0.005, 0.01, 0.05, 0.1, 0.5, 1, 2, 3, 4, 5 ml.

EXAMPLES

Some precursors are referred to by a nomenclature of naxxKpppfff, where n is the number of arms, xx is the molecular weight (MW), ppp is the polymer, and fff is the functional end group. Thus 8a15KPEGSAP refers to an 8-armed Polyethylene glycol (PEG) with a MW of 15,000 g/mol=15K PEG. Succinimidyl adipate is: SAP. Succinimidyl glutarate is SG. Succinimidyl azelate is: SAZ.

Example 1

This example relates to assess the swelling and persistence of a 5% and 10% PEG formulation. It provides an injectable solution that would maintain shape and mechanical integrity within a space until it gels, whether that space be a vitreous body, or other location. The precursors have good syringeability and good cohesion characteristics. Hyaluronic acid (HA) is a high molecular weight non-newtonian linear molecule; it enhanced viscosity of the precursor solution and performed well under high shear situations (passage through a thin gauge needle). A variety of different dilutions of 850 kDa HA was tested, with about 1% being suitable in this case. The buffers used to dissolve each precursor made a neutral pH when mixed, and the buffer with the SAZ precursor must be of low pH in order to maintain stability of the polymer in solution (avoid prehydrolysis). Each of these components, when mixed together, maintained its shape stability and volume stability, keeping its shape and position in a space until forming a hydrogel in 2-3 minutes (Table 3).

Procedure:
4.8% PEG formulation

Two stock buffers were made up to be used to dissolve each PEG:
  Preparation of 10 mL of the PEG amine buffer (to be used with the 8a20k $NH_3^+$):
  105 mg of Sodium tetraborate decahydrate into 10.0 mL of WFI, vortexed until in solution.
  200 mg of 850 kDa HA into 9.8 mL of Borate/WFI solution in a TD20 stirring apparatus.
Stirred at 6000 RPM for 15 minutes (until totally in solution)
  Preparation of 10 mL of the PEG ester buffer (to be used with the 4a20k SAZ):
  70 mg of Sodium phosphate monobasic into 10.0 mL of WFI, vortexed until in solution
  32 mg of 8a20k $NH_3^+$ into a 3 mL Beckton Dickinson (BD) syringe then connected luer to luer with 968 µL of PEG amine buffer. Added buffer into powder and mixed between syringes until in solution
  64 mg of 4a20k SAZ into a 3 mL BD syringe then connected luer to luer with 946 µL of PEG ester buffer. Added buffer into powder and mixed between syringes until in solution 500 mg of 8a20k NH$_3^+$ solution into a 3 mL BD syringe connected luer to luer with 500 mg of 4a20k SAZ solution, mixed back and forth for 30 seconds and dispensed onto aluminum weight boat for gel time testing. Depots are called gels when they begin to adapt a solid state and are no longer a liquid.

Gel time was broad and anywhere between 2:30 min and 3:00 min 9.6% PEG formulation Two stock buffers were made up to be used to dissolve each PEG:
  Preparation of 10 mL of the PEG amine buffer (to be used with the 8a20k NH$_3^+$):
  105 mg of Sodium tetraborate decahydrate into 10.0 mL of WFI, vortexed until in solution.
  200 mg of 850 kDa HA into 9.8 mL of Borate/WFI solution in a TD20 stirring apparatus.
Stirred at 6000 RPM for 15 minutes (until totally in solution)
  Preparation of 10 mL of the PEG ester buffer (to be used with the 4a20k SAZ):
  70 mg of Sodium phosphate monobasic into 10.0 mL of WFI, vortexed until in solution
  64 mg of 8a20k NH$_3^+$ into a 3 mL BD syringe then connected luer to luer with 946 µL of PEG amine buffer. Added buffer into powder and mixed between syringes until in solution
  128 mg of 4a20k SAZ into a 3 mL BD syringe then connected luer to luer with 872 µL of PEG ester buffer. Added buffer into powder and mixed between syringes until in solution
  500 mg of 8a20k NH$_3^+$ solution into a 3 mL BD syringe connected luer to luer with 500 mg of 4a20k SAZ solution, mixed back and forth for 30 seconds and dispensed onto aluminum weight boat for gel time testing. Depots are called gels when they begin to adapt a solid state and are no longer a liquid.

TABLE 3

Showing components and concentrations of formulations.
Gel time was 2:30-3:00 min

| | Formulation | |
|---|---|---|
| | 1 | 2 |
| PEG | 4a20k SAZ, 8a20k NH$_3^+$ | 4a20k SAZ, 8a20k NH$_3^+$ |
| % PEG | 4.80% | 9.60% |
| % HA | 1% (850 kDa) | 1% (850 kDa) |
| Buffer (Ester) | 7 mg/mL Monobasic (pH 4.0) | 7 mg/mL Monobasic (pH 4.0) |
| Buffer (Amine) | 10.5 mg/mL Borate (w/2% HA) | 10.5 mg/mL Borate (w/2% HA) |
| Gel Time | 2:30-3:00 min | 2:30-3:00 min |

Observation:
At 4.8% PEG, there is a linear relationship between borate concentration and gel time, which allows for a good target range for that syringe:
  $y = -0.2223x + 2.6816$ where x=[borate] and y=gel time
  10.7 mg/mL (2 min GT)≥x≥9.35 mg/mL (4 min GT)
Swelling and Dimensional Analysis:
  FIGS. 7 and 8 depict plots of swelling and dimensional change, respectively, for hydrogel depots placed in vitro in physiological buffer solution (PBS). It was further observed that, as the hydrogels degraded, they continued to swell in a linear trend upwards to 1000% before liquefying For swelling preparation, formulations were cast in 2 mmID silicon tubing and left to cure at a 100% RH environment at 37 C for 24 hours before being placed in 1xPBS pH 7.2. Depots were massed at t=1 hr and 24 hr to catch the burst, then less frequently after that.

For dimensional analysis, formulation 2 (9.8% PEG) was cast in a 2 mmID silicon tubing and left to cure at a 100% RH environment at 37 C for 24 hrs before being placed in 1xPBS pH 7.2. Most dimensional changes occur within the first hour.

Example 2

1 Dry Syringe, 1 Wet Syringe

Procedure:
  20% Dexamethazone loaded, 10% PEG formulation (all-in-one formulation) Preparation of 4a20K SAZ/8a20K NH$_3^+$ suspension in Dimethyl carbonate (DMC):
    Performed the following preparation under dry conditions
    1.00 g of 4a20k SAZ into a preweighed 10 mL serum vial
    Addition of 0.50 g of 8a20K NH$_3^+$ into the same serum vial
    Serum vial is then sealed with rubber stopper. Using a volumetric syringe, added 8.50 mL of DMC
    Vortexed the vial until the suspension appeared homogenous
  Preparation of Syringes with Dexamethasone powder:
    40 mg of Dexamethasone powder was weighed into a 1 mL Soft-ject syringe
    133 µL of previously prepared 4a20K SAZ/8a20K NH$_3^+$ suspension in Dimethyl carbonate was added using a volumetric syringe and needle through the luer of the Soft-ject syringe.
    Syringe was then capped and immediately frozen on a customized tote (−50 C)
    Once frozen, syringe cap was removed and tote was placed in lyophilizer.
    Syringe was then freeze dried overnight to remove any residual solvents.
  Preparation of Diluent:
    2.56 g of Monobasic sodium phosphate, 2.56 g of Dibasic sodium phosphate, 8.50 g of Sodium Chloride, and 0.50 g of Sodium tetraborate decahydrate were added into a 1 L volumetric flask and brought to volume using WFI.
    pH of the solution was then adjusted to 6.8 using 6N hydrochloric acid.
    To make diluent, 400 µL of the prepped buffer solution was mixed syringe to syringe with 1600 µL of Provisc (1% HA 2000 kDa) which resulted in a 2 mL stock diluent solution.
  Creation of gel:
    Dry syringe with 40 mg of Dexamethasone and 20 mg of dry PEG powders (4a20K SAZ/8a20K NH$_3^+$) was mixed with 140 µL of prepared diluent solution for about 30 seconds
    Resulting suspension was dispensed onto an aluminum weight boat for gel time testing.
    Depots are called gels when they begin to adapt a solid state and are no longer a liquid.
Gel time for these depots are between 3-6 minutes.
In Vivo Injections:
  20% Dex formulation (with fluoresceinated Amine) used for in vivo injections at PARF. 25 µL were injected using a 50 µL Hamilton syringe with the 27G ½" RN. Formulation is extremely syringeable. Some depots were left in for in vivo release. One depot was explanted immediately after injection for in vitro release (tracking dex clearance visually); results are shown in FIG. 9. The depot was placed in an excess of PBS for the indicated time, photographed, and observed for release of the agent. The matrix was fluoresceinated and had a yellow appearance. The presence of the agent made the matrix appear opaque. As the agent was released, the depot became more translucent. The depot is thicker in its central portions and, in the images, the coloration of the matrix gives it an appearance of being more opaque. The release of the agent is most easily observed in the edges.

Example 3

Dexamethasone Intravitreal Depot

This example details a process that could be used for making and testing or using a hydrogel for release of an agent.
A. The following components are mixed:
  20 mg 4 arm 20 K PEG SAZ
  10 mg 8 arm 20 K PEG amine HCl salt
  30 mg of micronized dexamethasone
  240 mg dimethyl carbonate
The mixture is lyophilized to form a dried lyophilizate.
B. An aqueous buffer solution is prepared as follows:
  8 mg/mL sodium hyaluronate (850 KDa)
  0.1 mg/mL sodium tetraborate decahydrate
  0.51 mg/mL sodium phosphate monobasic
  0.51 mg/mL sodium phosphate dibasic
  1.7 mg/mL sodium chloride
  adjust pH to 6.8 using 6N hydrochloric acid solution
  Combine 10 mg of A with 40 mg of B in a syringe and inject into the posterior chamber of an eye. A roughly spheroidal shape is formed in the eye, which solidifies into a hydrogel in approximately 2 to 5 minutes. The dexamethasone is slowly released into the vitreous fluid and gradually transfers into the adjoining tissues, e.g. retina, ciliary body, anterior chamber and choroid for therapeutic benefit.

Example 4

Loteprednol Etabonate Intravitreal Depot

This example details a process that could be used for making and testing or using a hydrogel for release of an agent.
A. The following components are mixed:
  20 mg 4 arm 20 K PEG SAZ
  10 mg 8 arm 20 K PEG amine HCl salt
  30 mg of micronized dexamethasone
  240 mg dimethyl carbonate
The mixture is lyophilized to form a dried lyophilizate.
B. An aqueous buffer solution is prepared as follows:
  8 mg/mL sodium hyaluronate (850 KDa)
  0.1 mg/mL sodium tetraborate decahydrate
  0.51 mg/mL sodium phosphate monobasic
  0.51 mg/mL sodium phosphate dibasic
  1.7 mg/mL sodium chloride
  adjust pH to 6.8 using 6N hydrochloric acid solution
  Combine 10 mg of A with 40 mg of B in a syringe and inject into the posterior chamber of an eye. A roughly spheroidal shape is formed in the eye, which solidifies into a hydrogel in approximately 2 to 5 minutes. The loteprednol etabonate is slowly released into the vitreous fluid and gradually transfers into the adjoining tissues, e.g. retina, ciliary body, anterior chamber and choroid for therapeutic benefit.

Example 5

Axitinib Intravitreal Depot

This example details a process that could be used for making and testing or using a hydrogel for release of an agent.
A. The following components are mixed:
  20 mg 4 arm 20 K PEG SAZ
  10 mg 8 arm 20 K PEG amine HCl salt
  30 mg of micronized loteprednol etabonate
  240 mg dimethyl carbonate
The mixture is lyophilized to form a dried lyophilizate.
B. An aqueous buffer solution is prepared as follows:
  8 mg/mL sodium hyaluronate (850 KDa)
  0.1 mg/mL sodium tetraborate decahydrate
  0.51 mg/mL sodium phosphate monobasic
  0.51 mg/mL sodium phosphate dibasic
  1.7 mg/mL sodium chloride
  adjust pH to 6.8 using 6N hydrochloric acid solution
  Combine 10 mg of A with 40 mg of B in a syringe and inject into the posterior chamber of an eye. A roughly spheroidal shape is formed in the eye, which solidifies into a hydrogel in approximately 2 to 5 minutes. The axitinib is slowly released into the vitreous fluid and gradually transfers into the adjoining tissues, e.g. retina, ciliary body, anterior chamber and choroid for therapeutic benefit.

Example 6

Axitinib Intravitreal Depot with Triggered Gelation

This example details a process that could be used for making and testing or using a hydrogel for release of an agent.
A. The following components are mixed:
  20 mg 4 arm 20 K PEG SAZ
  10 mg 8 arm 20 K PEG amine HCl salt
  30 mg of micronized loteprednol etabonate
  240 mg dimethyl carbonate
The mixture is lyophilized to form a dried lyophilizate.
B. An aqueous solution is prepared as follows:
  8 mg/mL sodium hyaluronate (850 KDa)
  1.7 mg/mL sodium chloride
C. An aqueous solution is prepared as follows:
  0.1 mg/mL sodium tetraborate decahydrate
  0.51 mg/mL sodium phosphate monobasic
  0.51 mg/mL sodium phosphate dibasic
  50 mg/mL polyethylene glycol (8 KDa)
  Coat a polyethylene tube, length 3.25 mm, outer diameter 3.02 mm, inner diameter 1.26 mm with C and allow to dry, forming a film coating on all surfaces. Place the coated tubing in the hub of a Nipro 30 gauge thin wall Leur Lok needle.
  Combine 10 mg of A with 40 mg of B in a syringe and attach the needle containing the coated tube. In a smooth motion over approximately 2 seconds, inject the syringe contents into the posterior chamber of an eye. A roughly spheroidal shape is formed in the eye, which solidifies into a hydrogel in approximately 2 to 5 minutes. The axitinib is slowly released into the vitreous fluid and gradually transfers into the adjoining tissues, e.g. retina, ciliary body, anterior chamber and choroid for therapeutic benefit.

Example 7

Axitinib Intravitreal Depot with Triggered Gelation

This example details a process that could be used for making and testing or using a hydrogel for release of an agent.

A. The following components are mixed:
- 20 mg 4 arm 20 K PEG SAZ
- 10 mg 8 arm 20 K PEG amine HCl salt
- 30 mg of micronized loteprednol etabonate
- 240 mg dimethyl carbonate The mixture is lyophilized to form a dried lyophilizate.

B. An aqueous solution is prepared as follows:
- 11 mg/mL sodium hyaluronate (850 KDa)
- 2.3 mg/mL sodium chloride C. An aqueous solution is prepared as follows:
- 0.4 mg/mL sodium tetraborate decahydrate
- 2.0 mg/mL sodium phosphate monobasic
- 2.0 mg/mL sodium phosphate dibasic Combine 10 mg of A with 30 mg of B in the larger lumen of a two-barrel syringe with a 2:1 barrel radius ratio and a needle containing a static mixing element. In a smooth motion over approximately 2 seconds, inject the syringe contents into the posterior chamber of an eye. A roughly spheroidal shape is formed in the eye, which solidifies into a hydrogel in approximately 2 to 5 minutes. The axitinib is slowly released into the vitreous fluid and gradually transfers into the adjoining tissues, e.g. retina, ciliary body, anterior chamber and choroid for therapeutic benefit.

Example 8

Axitinib Intravitreal Depot

This example details a process that could be used for making and testing or using a hydrogel for release of an agent.

A. The following components are mixed:
- 20 mg 4 arm 20 K PEG SAZ
- 10 mg 8 arm 20 K PEG amine HCl salt
- 30 mg of micronized axitinib
- 240 mg dimethyl carbonate The mixture is lyophilized to form a dried lyophilizate.

B. An aqueous solution is prepared by adjusting the pH of water for injection 4.0 using 0.1N hydrochloric acid solution Combine 10 mg of A with 40 mg of B in a syringe and inject into the posterior chamber of an eye. A roughly spheroidal shape is formed in the eye, which gradually solidifies into a hydrogel as the local pH increases to equal the vitreous fluid pH, about 7.2. The axitinib is slowly released into the vitreous fluid and gradually transfers into the adjoining tissues, e.g. retina, ciliary body, anterior chamber and choroid for therapeutic benefit.

Example 9

Preparation and Testing of Kits

Preparation of envelope PEG and anhydrous dimethyl carbonate suspension
- 500 mg of 4 arm 20 k SAZ was massed into a pre-weighed vial
- 250 mg of 8 arm 20 k $NH_3^+$ was massed into the same vial
- 9.25 mL of anhydrous dimethyl carbonate was added to the powders under Nitrogen until suspension was homogenous (this created a 5%: 2.5% 4 arm 20 k SAZ: 8 arm 20 k $NH_3^+$ preparation)
- 2.5 mL of PEG/DMC suspension was poured into a small aluminum weigh boat
- Weight boat was then placed on a cold aluminum surface (recently removed from a −40° C. freezer) placed under the glove bag so that the PEG/DMC could freeze without exposure to atmosphere
- Still frozen, weigh boat was transferred to lyophilizer shelf and cycle was run to remove all solvent.

Preparation of PEG in Needle Hub:
- 27G ½" needles were pre-weighed on balance in dry conditions
- Previously prepared PEG powder was transferred into the needle hub by using the needle as a biopsy punch (target was between 3-6 mg of PEG)
- 4.96 mg of envelope PEG was weighed out into a needle. This was placed aside for future use.

Preparation of Xerogel:
The following components were dissolved in dimethyl carbonate:
- 11.4% 8 arm 20 k NH2 in DMC
- 8.6% 8 arm 15 k SG in DMC
- 1600 mg of anhydrous microfine lactose from DFE Pharma was suspended in 4200 μL of 11.4% 8 arm 20 k NH2 (above)
- This syringe was mixed syringe to syringe with 4200 μL of 8.6% 8 arm 15 k SG until bulk gel was formed.
- Particle size of the bulk gel was then reduced by running through homogenizer.
- Particles were then dried using a filter drier to remove DMC and fines
- Final particle size was a d50 of 430 um Preparation of Diluent:
- Monobasic sodium phosphate, Dibasic sodium phosphate, Sodium tetraborate decahydrate were added into a 1 L volumetric flask and brought to volume using water.
- pH of the solution was then adjusted to 7.2 using 6N hydrochloric acid.
- To make diluent, 1120 μL of the prepped buffer solution was mixed syringe to syringe with 880 μL of Provisc (1% HA 2000 kDa), which resulted in a 2 mL stock diluent solution Preparation of Hydrogel Slurry:
- 212 mg of a previously prepared xerogel (above) was massed into a syringe
- 1.829 g of previously prepared diluent (above) was then added syringe to syringe and hydrogel suspension was mixed until fully homogenous.

Injection and Gelation:
Table 4 shwoing each preparation including kit components and resulting gel times. Gelation is achieved by injecting the slurry through the needle onto an aluminum weigh boat.

| Kit: | PEG (needle) | Slurry | Gel Time |
|---|---|---|---|
| 1 | 4.44 mg | 70 μL | 3:00 min |
| 2 | 4.85 mg | 80 μL | 2:40 min |
| 3 | 5.49 mg | 87 μL | 2:40 min |
| 4 | 5.65 mg | 90 μL | 2:50 min |
| 5 | 6.14 mg | 98 μL | 2:30 min |
| 6 | 4.96 mg | 80 μL | 2:45 min |
| 7 | 3.76 mg | 60 μL | 2:30 min |

Example 10

Steroid Candidates

1. Flunisolide, anhydrous, USP
2. Micronized budesonide
3. Betamethasone sodium phosphate, USP
4. Triamcinolone acetonide, powder, USP Steroid Solubility Studies Solubility of the steroid candidates was assessed in dissolution media (PBS, pH 6.3) at ambient temperatures for 68 hours. UV detection of soluble steroid was determined relative to a standard curve. The maximal determined solubility is shown below:

Flunisolide Max Solubility in PBS, pH 6.3=90 µg/mL (245 nm)

Betamethasone Sodium Phosphate Max Solubility in PBS, pH 6.3=>100,000 µg/mL (freely soluble in water) (241 nm)

Budesonide Max Solubility in PBS, pH 6.3=30 µg/mL (247 nm)

Triamcinolone Acetonide Max Solubility in PBS, pH 6.3=20 µg/mL (241 nm)

Depot Formulation

Syringe 1: 10 mg of steroid was and 42 mg of 4-arm 20,000 molecular weight PEG succinimidyl glutarate (4a20KSG) was weighed into the syringe and then dissolved in 233 µL of 1 mg/mL sodium phosphate monobasic containing 1 mg of trilysine (LLL). The low pH (~4.5) prevents reactivity between the PEG and LLL components.

Syringe 2: 6 mg of sodium tetraborate was weighed into a syringe and dissolved in 233 µL of water for injection (WFI).

The two syringes were mixed between the syringes using a luer connector and injected into a 10 mm borosilicate tube containing a small stir bar over a stir plate. The mixing prevented settling of the steroid suspension until sufficient viscosity was achieved during hydrogel formation. This resulted in an approximate 0.45 mL volume of 10 mg of steroid entrapped with a 9% hydrogel (w/v). A visual representation of the depot shape is shown in FIG. 10.

Release Rate from In Vitro Depots

The release rate from the 10 mg steroid containing hydrogel depots in 1 L of PBS, pH 6.3 at ambient temperature with gentle stirring was performed for each steroid candidate and compared to the dissolution profile of 10 mg of neat drug dispersed in an equal volume of dissolution media (FIG. 11). A visual representation of drug release from the depots over time is observed in FIG. 12 for the flunisolide steroid candidate.

Example 11

In a similar construct, lotepredenol etabonate, dexamethasone, micronized dexamethasone, prednisolone and prednisolone acetate were suspended in PEG hydrogel precursor solutions and injected into tubing and allowed to gel as covalently crosslinked hydrogels and then cut into barrel shaped depots. The steroid suspended gels were removed from the tubing and ex vivo release was initiated in dissolution media. Zone clearance (steroid released) from the depot interface inward was observed and visually recorded. See FIGS. 13-16.

Example 12

100 µg Micronized Axitinib Suspension Injection

Buffer Preparation

10×PBS (VWR International) was diluted 1:10 with water and the pH was brought to 7.2 using 0.01N NaOH and 0.01N HCl. This solution was then filtered at a rate of 2 mL/min through a 0.2 µm filter to remove any endotoxin or bioburden.

Creating the Suspension

200 µg of micronized axitinib was weighed into a 50 mL amber vial. It was dried, stoppered and crimped, and gamma irradiation sterilized. After irradiation, 9.80 mL of buffer was added to the vial. The suspension was then placed in a sonication bath for 20 minutes to homogenously disperse the micronized particles.

Injection of Material

50 µL of the 2% axitinib suspension was then drawn into a 100 µL luer lock Hamilton syringe using a 21G 1.5" needle. The needle was swapped for a fresh 27G ½" TW needle (Nipro). The 50 µL suspension was then injected at the 6 o'clock position within the vitreous of a Male New Zealand white rabbit. After 1 month, eyes were explanted and prepared for histology.

Histology Method

Two eyes were fixed (Davidson's), blocked, sectioned, mounted and stained for microscopical examination by a board certified veterinary pathologist. Eyes were sectioned according to the following scheme: A suture had been placed at the 12 o'clock position for orientation at harvest. Typically eyes were trimmed in half in the plane from 12 o'clock to 6 o'clock through the lens and optic nerve along the midline. This captures as many optic structures in one plane as is possible. The trimmed eyes were examined grossly and abnormalities noted. Each half of the globe trimmed was embedded in its own cassette. Cassette A is always the nasal half of the eye, and cassette B is always the temporal half of the eye. For each block 6 hematoxylin and eosin (H&E)-stained slides were prepared that were separated by 1000 microns (1 mm). Each slide contained 2 serial sections of eye on it. All slides were evaluated by a board-certified veterinary pathologist at Charter Preclinical Services. Tissues were scored on a semi-quantitative scale from 0-5 for any abnormalities.

Eyes were scored in several categories for signs of inflammation or other adverse findings. Inflammation scores were as follows:

0—No change; normal
1—Rare foci of change; minimal
2—Mild diffuse change or more pronounced focal change
3—Moderate diffuse change
4—Marked diffuse change
5—Severe diffuse change Histology Result:

Inflammation within the vitreous Chamber: 0.0±0.0
Inflammation around the injected material: 0.04±0.29
Other adverse findings (retina, sclera, lens, etc.): none

Example 13

200 µg Micronized Axitinib Suspension Injection

Axitinib Dissolution 195 mg of Axitinib (manufactured by LGM Pharma, GMP grade) was dissolved into 110 mL of Ethanol (Sigma Aldrich) in a glass serum vial, capped and crimped (1.77 mg Axitinib/mL ethanol). This vial was then wrapped in aluminum foil to protect the solution from light, and sonicated until completely dissolved. Solution was then aspirated into two 60 mL polyethylene (PE) luer-lok syringes (BD) wrapped in aluminum foil.

Axitinib Precipitation 1800 mL of sterile Water For Injection (WFI) was measured into a 2 L beaker and placed on a stir plate stirring at 600 RPM with a stir bar, creating a large WFI vortex in the center of the beaker. One 60 mL BD syringe containing axitinib in ethanol was placed on a syringe pump which had been clamped above the WFI beaker. A hypodermic needle (21G, BD) was connected to the syringe and aimed directly into the center of the vortex for dispensation of the axitinib solution. The axitinib solution was added dropwise to the WFI to precipitate micronized Axitinib.

Axitinib Suspension Filtration and Collection

After micronization, the Axitinib suspended in 5.7% ethanol/94.3% WFI was filtered through a 0.2 um vacuum filter (Thermo Scientific) and rinsed 3× with 100 mL of WFI. After filtration, Axitinib powder was collected from the filter using a spatula, and vacuum dried overnight in a 10 mL serum vial to remove all excess solvent.

Particle Size Analysis

Particle size was analyzed using a Beckman Coulter LS 120 Particle Size Analyzer. Samples were sonicated for 15 minutes in Deionized water before analysis. On average the particle size distribution is such: d10=0.773 um, d50=2.605 um, d90=6.535 um.

Creating the Suspension

40 μg of micronized Axitinib was weighed into a sterile 3 mL BD luer lock syringe. 960 μL of Provisc (Alcon, Inc., 1% 2000 kDa Hyaluronic acid solution) was added to a fresh 3 mL BD luer lock syringe. The two syringes were mixed using a luer connector.

Injection of Material

5 μL of the 4% Axitinib suspension was then drawn into a 100 μL luer lock Hamilton syringe using a 21G 1.5" needle. The needle was swapped for a fresh 27G ½" TW needle (Nipro). The 50 μL suspension was then injected at the 6 o'clock position within the vitreous of a Male New Zealand white rabbit. After 1 month, eyes were explanted and prepared for histology.

Histology Method

Two eyes were fixed (Davidson's fixative solution), blocked, sectioned, mounted and stained for microscopical examination by a board certified veterinary pathologist. Eyes were sectioned according to the following scheme: A suture had been placed at the 12 o'clock position for orientation at harvest. Typically eyes were trimmed in half in the plane from 12 o'clock to 6 o'clock through the lens and optic nerve along the midline. This captures as many optic structures in one plane as is possible. The trimmed eyes were examined grossly and abnormalities noted. Each half of the globe trimmed was embedded in its own cassette. Cassette A is always the nasal half of the eye, and cassette B is always the temporal half of the eye. For each block 6 hematoxylin and eosin (H&E)-stained slides were prepared that were separated by 1000 microns (1 mm). Each slide contained 2 serial sections of eye on it. All slides were evaluated by a board-certified veterinary pathologist at Charter Preclinical Services. Tissues were scored on a semi-quantitative scale from 0-5 for any abnormalities.

Eyes were scored in several categories for signs of inflammation or other adverse findings as described above.

Histology Result

Inflammation within the vitreous Chamber: 0.14±0.35
Inflammation around the injected material: 0.08±0.37
Other adverse findings (retina, sclera, lens, etc.): none Example 14

400 ug Micronized Axitinib Suspension Injection

Axitinib Dissolution 195 mg of Axitinib (manufactured by LGM Pharma, GMP grade) was dissolved into 110 mL of Ethanol (Sigma Aldrich) in a glass serum vial, capped and crimped (1.77 mg Axitinib/mL ethanol). This vial was then wrapped in aluminum foil to protect the solution from light, and sonicated for 20 minutes until completely dissolved. Solution was then drawn into two 60 mL polyethylene (PE) luer-lok syringes (BD) wrapped in aluminum foil.

Axitinib Precipitation 1800 mL of sterile Water For Injection (WFI) was measured into a 2 L beaker and placed on a stir plate stirring at 600 RPM with a stir bar, creating a large WFI vortex in the center of the beaker. One 60 mL BD syringe containing axitinib in ethanol was placed on a syringe pump which had been clamped above the WFI beaker. A hypodermic needle (21G, BD) was connected to the syringe and aimed directly into the center of the vortex for dispensation of the axitinib solution. The syringe pump was then run at 7.5 mL/min in order to add the axitinib solution dropwise to the WFI to precipitate micronized Axitinib.

Axitinib Suspension Filtration and Collection

After micronization, the Axitinib suspended in 5.7% ethanol/94.3% WFI was filtered through a 0.2 um vacuum filter (Thermo Scientific) and rinsed 3× with 100 mL of WFI. After filtration, Axitinib powder was collected from the filter using a spatula, and vacuum dried overnight in a 10 mL serum vial to remove all excess solvent.

Particle Size Analysis

Particle size was analyzed using a Beckman Coulter LS 120 Particle Size Analyzer. Samples were sonicated for 15 minutes in Deionized water before analysis. On average the particle size distribution is such: d10=0.773 um, d50=2.605 um, d90=6.535 um.

Creating the Suspension

80 μg of micronized Axitinib was weighed into a sterile 3 mL BD luer lock syringe. 920 μL of Provisc (Alcon, Inc., 1% 2000 kDa Hyaluronic acid solution) was added to a fresh 3 mL BD luer lock syringe. The two syringes were mixed using a luer connector.

Injection of Material

50 μL of the 8% axitinib suspension was then drawn into a 100 μL luer lock Hamilton syringe using a 21G 1.5" needle. The needle was swapped for a fresh 27G ½" TW Nipro needle. The 50 μL suspension was then injected at the 6 o'clock position within the vitreous of both eyes in Male New Zealand white rabbit. After 1 month, eyes were explanted and prepared for histology.

Histology Method

Two eyes were fixed (Davidson's fixative solution), blocked, sectioned, mounted and stained for microscopical examination by a board certified veterinary pathologist. Eyes were sectioned according to the following scheme: A suture had been placed at the 12 o'clock position for orientation at harvest. Typically eyes were trimmed in half in the plane from 12 o'clock to 6 o'clock through the lens and optic nerve along the midline. This captures as many optic structures in one plane as is possible. The trimmed eyes were examined grossly and abnormalities noted. Each half of the globe trimmed was embedded in its own cassette. Cassette A is always the nasal half of the eye, and cassette B is always the temporal half of the eye. For each block 6 hematoxylin and eosin (H&E)-stained slides were prepared that were separated by 1000 microns (1 mm). Each slide contained 2 serial sections of eye on it. All slides were evaluated by a board-certified veterinary pathologist at Charter Preclinical Services. Tissues were scored on a semi-quantitative scale from 0-5 for any abnormalities.

Eyes were scored in several categories for signs of inflammation or other adverse findings as described above.
Histology Result
  Inflammation within the vitreous Chamber: 0.14±0.35
  Inflammation around the injected material: 0.14±0.35
  Other adverse findings (retina, sclera, lens, etc.): none
Further Disclosure 1. A method of agent delivery to a tissue comprising forming a hydrogel implant in situ with a therapeutic agent in the hydrogel (e.g., dissolved, suspended, dispersed throughout), the agent having a low solubility or a very low solubility in water. The site may be, e.g., in an eye, in an eye tissue, intracameral, or intravitreal.

2. The method of 1 wherein the hydrogel is water-degradable, as measurable by the hydrogel being dissolvable in vitro in an excess of water by degradation of water-degradable groups.

3. The method of 1 or 2 wherein the hydrogel essentially persists until the agent is essentially released.

4. The method of 1 or 2 with 50% to 100% w/w (Artisans will immediately appreciate that all ranges and values between the explicitly stated bounds are contemplated, with, e.g., any of the following being available as an upper or lower limit: 55%, 60%, 65%, 70%, 75% 80%, 85%, 90%, 95%, or 99%, e.g., 90% to 99%, or 55% to 99%) of the agent being released when the hydrogel is from 100% to 90% persistent. Alternatively, when the hydrogel is from 100% to 80% persistent.

5. The method of any of 1-4 wherein the hydrogel delivers the agent at a therapeutically effective concentration for a period of time that is in a range of 1-36 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months. Shorter periods of time could also be used, e.g., 1-31 days; Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 20, 25, 30, or 31 days.

6. The method of 5 wherein, after the period of time, the hydrogel has released all of the agent and is at least 80% persistent.

7. The method of 5 wherein, after the period of time, the hydrogel releases an amount of the agent that is non-toxic.

8. The method of 5 or 7 wherein the hydrogel delivers a final 1%-20% w/w of the agent after the period of time. Artisans will immediately appreciate that all ranges and values between the explicitly stated bounds are contemplated, with, e.g., any of the following being available as an upper or lower limit: 1, 2, 3, 4, 5, 10, 15, 16, 17, 18, 19% w/w.

9. The method of any of 1-8 wherein the hydrogel delivers a final 1%-20% w/w of the agent by degradation of the hydrogel. Artisans will immediately appreciate that all ranges and values between the explicitly stated bounds are contemplated, with, e.g., any of the following being available as an upper or lower limit: 1, 2, 3, 4, 5, 10, 15, 16, 17, 18, 19% w/w.

10. The method of any of 1-9 wherein the hydrogel is no more than 10% degraded (alternatively no more than 15%, 20%, or 25% degraded) for a time that is in a range of 1-36 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months.

11. The method of any of 1-10 wherein 50% w/w$_i$ of the agent delivered is at time that is in a range of 1-20 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, or 20 months.

12. The method of any of 1-11 wherein 50% w/w$_i$ of the hydrogel is degraded at a time that is 1-20 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, or 20 months.

13. The method of any of 1-12 wherein the tissue and/or the site of formation of the hydrogel is an eye, intracanalicular, sub-tenons, intracameral, intravitreal, intrasceleral, choroidal, suprachoroidal, a retina, subretinal, a lens, a tissue, lumen, void, potential space, inside an animal (human or otherwise), or on a surface of an animal, iatrogenic site, site where tissue is removed, surgical site, cancer tissue, at or near cancer tissue, dental tissue, gums, periodontal, sinus, brain, intravascular, aneurysm, or site of a pathology.

14. The method of any of 1-13 wherein the agent is for treatment of a back of the eye disease.

15. The method of 14 wherein the back of the eye disease is age-related macular degeneration (AMD) cystoid macular edema (CME), diabetic macular edema (DME), posterior uveitis, diabetic retinopathy, retinal vein occlusion, or glaucoma.

16. The method of any of 1-15 wherein the tissue is a retina, lens, cornea, or sclera.

17. The method of any of 1-16 wherein the agent comprises anti-VEGF, blocks VEGFR1, blocks VEGFR2, blocks VEGFR3, anti-PDGF, anti-PDGF-R blocks PDGFRβ, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib Bosutinib Neratinib, lapatinib, or Vatalanib. Also wherein the agent is a steroid, nonsteroidal antiinflammatory drug, antibiotic, or pain killer 18. The method of any of 1-17 wherein the agent comprises low-soluble prostaglandin analogues for glaucoma, Nepafenac for uveitis, Macrolides, such as rapamycin, sirolimus, tacrolimus, to block mTOR receptors for AMD/CNV 19. The method of any of 1-18 wherein the agent is a suspension (liquid or solid) in the hydrogel. For example: particles of the agent or drops of the agent, the particles or drops being microscopic (1-500 microns diameter) and/or nanoscopic (less than 1 micron diameter).

20. The method of any of 1-19 wherein the agent is dispersed throughout the hydrogel.

21. The method of any of 1-20 wherein a volume of the hydrogel is from 1 to 1000 µL. Artisans will immediately appreciate that all ranges and values between the explicitly stated bounds are contemplated, with, e.g., any of the following being available as an upper or lower limit: 1, 10, 20, 50, 100, 200, 300, 400, 500, 900, 1000 µL.

22. The method of any of 1-21 wherein the hydrogel is a first hydrogel, the method further comprising forming a second hydrogel in situ with a second agent in the second hydrogel, the second agent optionally having a low solubility in water.

23. The method of 22 wherein the first agent and the second agent have the same active ingredient.

24. The method of 22 or 23 wherein the first agent and the second agent comprise different enantiomers, salts, or free bases.

25. The method of 22 or 23 wherein the first agent and the second agent have identical chemical structures.

26. The method of any of 22-25, with the first hydrogel releasing the agent more quickly than the second hydrogel.

27. The method of any of 22-26 with the first hydrogel having a larger surface area than the second hydrogel.

28. The method of any of 22-27 with the first hydrogel providing a faster rate of diffusion for the agent relative to the second hydrogel.

29. The method of any of 22-28 wherein the first agent and the second agent are different chemical moieties.

30. The method of any of 22-29 wherein the hydrogel is formed by combining a first precursor and a second precursor that react with each other to form the hydrogel.

31. The method of 30 wherein the hydrogel is formed without covalent crosslinks between the first precursor and the second precursor.

32. The method of any of 1-31 wherein the hydrogel is formed by combining a first precursor comprising nucleophilic groups with a second precursor comprising electrophilic groups to form covalent crosslinks by reaction of the nucleophilic groups with the electrophilic groups to form the hydrogel.

33. The method of any of 30-32 comprising injecting an aqueous mixture of the precursors to the site.

34. The method of any of 30-33 wherein the first precursor and the second precursor are hydrophilic.

35. The method of any of 30-34 wherein the first precursor and/or the second precursor comprise poly(ethylene) glycol repeats.

36. The method of any of 1-35 further comprising hyaluronic acid or hydrophilic polymers that do not form part of a matrix of the hydrogel.

37. The method of any of 1-36 comprising activating a precursor to form the hydrogel.

38. The method of any of 1-37 comprising mixing a plurality of precursors to start a chemical reaction between the plurality of precursors, with the plurality of precursors reacting with each other to form the hydrogel.

39. The method of any of 32-38 wherein the precursors are activated and/or mixed before, after, or during placement at the site.

40. The method of any of 1-39 further comprising a buffering agent.

41. The method of 40 wherein the buffering agent is a solid.

42. The method of 41 wherein the solid is disposed in an applicator for placing a hydrogel precursor at the site, with the precursor contacting the solid as the precursor is passed through the applicator.

43. The method of 41 or 42 wherein the solid is disposed in a lumen of the applicator that receives the precursor, is disposed in a hub of a needle, is disposed in a syringe, or is a pellet for placement in an/the applicator.

44. The method of any of 40-43 wherein the buffering agent comprises a phosphate, bicarbonate, or carbonate.

45. The method of any of 1-44 wherein the site and/or the tissue is a tumor, a damaged tissue, a diseased tissue, an infected tissue, an organ, a vasculature, an adventitia, an artery, a vein, or a nerve.

46. The method of any of 1-45 wherein the hydrogel is elongate, spheroidal, spherical, essentially spherical, ellipsoidal, cylindroid, essentially cylindroid, discoidal, or essentially discoidal.

47. The method of any of 1-46 wherein the agent is delivered at an effective amount or a calculated effective amount.

51. A hydrogel implant with a therapeutic agent in the hydrogel (e.g., dissolved, suspended, dispersed throughout), the agent having a low solubility or a very low solubility in water. The site may be, e.g., in an eye, in an eye tissue, intracameral, or intravitreal.

52. The hydrogel of 51 wherein the hydrogel is water-degradable, as measurable by the hydrogel being dissolvable in vitro in an excess of water by degradation of water-degradable groups.

53. The hydrogel of 51 or 52 wherein the hydrogel essentially persists until the agent is essentially released.

54. The hydrogel of 51 or 52 with 50% to 100% w/w (Artisans will immediately appreciate that all ranges and values between the explicitly stated bounds are contemplated, with, e.g., any of the following being available as an upper or lower limit: 55%, 60%, 65%, 70%, 75% 80%, 85%, 90%, 95%, or 99%, e.g., 90% to 99%, or 55% to 99%) of the agent being released when the hydrogel is from 100% to 90% persistent. Alternatively, when the hydrogel is from 100% to 80% persistent. 55. The hydrogel of any of 51-54 wherein the hydrogel delivers the agent at a therapeutically effective concentration for a period of time that is in a range of 1-36 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months. Shorter periods of time could also be used, e.g., 1-31 days; Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 20, 25, 30, or 31 days.

56. The hydrogel of 55 wherein, after the period of time, the hydrogel has released all of the agent and is at least 80% persistent. 57. The hydrogel of 55 wherein, after the period of time, the hydrogel releases an amount of the agent that is non-toxic.

58. The hydrogel of 55 or 57 wherein the hydrogel delivers a final 1%-20% w/w of the agent after the period of time. Artisans will immediately appreciate that all ranges and values between the explicitly stated bounds are contemplated, with, e.g., any of the following being available as an upper or lower limit: 1, 2, 3, 4, 5, 10, 15, 16, 17, 18, 19% w/w.

59. The hydrogel of any of 1-8 wherein the hydrogel delivers a final 1%-20% w/w of the agent by degradation of the hydrogel. Artisans will immediately appreciate that all ranges and values between the explicitly stated bounds are contemplated, with, e.g., any of the following being available as an upper or lower limit: 1, 2, 3, 4, 5, 10, 15, 16, 17, 18, 19% w/w.

60. The hydrogel of any of 51-59 wherein the hydrogel is no more than 10% degraded (alternatively no more than 15%, 20%, or 25% degraded) for a time that is in a range of 1-36 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months.

61. The hydrogel of any of 51-60 wherein 50% w/w$_i$ of the agent delivered is at time that is in a range of 1-20 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, or 20 months.

62. The hydrogel of any of 51-61 wherein 50% w/w$_i$ of the hydrogel is degraded at a time that is 1-20 months after formation of the hydrogel in situ. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, 13, 14, 15, 16, 17, 18, 19, or 20 months.

63. The hydrogel of any of 51-62 wherein the tissue and/or the site of formation of the hydrogel is an eye, intracanalicular, sub-tenons, intracameral, intravitreal, intrasceleral, choroidal, suprachoroidal, a retina, subretinal, a lens, a tissue, lumen, void, potential space, inside an animal (human or otherwise), or on a surface of an animal, iatrogenic site, site where tissue is removed, surgical site, cancer tissue, at or near cancer tissue, dental tissue, gums, periodontal, sinus, brain, intravascular, aneurysm, or site of a pathology.

64. The hydrogel of any of 51-63 wherein the agent is for treatment of a back of the eye disease.

65. The hydrogel of 64 wherein the back of the eye disease is age-related macular degeneration (AMD) cystoid macular edema (CME), diabetic macular edema (DME), posterior uveitis, diabetic retinopathy, retinal vein occlusion, or glaucoma.

66. The hydrogel of any of 51-65 wherein the tissue is a retina, lens, cornea, or sclera.

67. The hydrogel of any of 51-66 wherein the agent comprises anti-VEGF, blocks VEGFR1, blocks VEGFR2, blocks VEGFR3, anti-PDGF, anti-PDGF-R blocks PDGFRβ, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib Bosutinib Neratinib, lapatinib, or Vatalanib. Also wherein the agent is a steroid, nonsteroidal antiinflammatory drug, antibiotic, or pain killer 68. The hydrogel of any of 51-67 wherein the agent comprises low-soluble prostaglandin analogues for glaucoma, Nepafenac for uveitis, Macrolides, such as rapamycin, sirolimus, tacrolimus, to block mTOR receptors for AMD/CNV 69. The hydrogel of any of 51-68 wherein the agent is a suspension (liquid or solid) in the hydrogel. For example: particles of the agent or drops of the agent, the particles or drops being microscopic (1-500 microns diameter) and/or nanoscopic (less than 1 micron diameter).

70. The hydrogel of any of 1-19 wherein the agent is dispersed throughout the hydrogel.

71. The hydrogel of any of 1-70 wherein a volume of the hydrogel is from 1 to 1000 µL. Artisans will immediately appreciate that all ranges and values between the explicitly stated bounds are contemplated, with, e.g., any of the following being available as an upper or lower limit: 1, 10, 20, 50, 100, 200, 300, 400, 500, 900, 1000 µL.

72. The hydrogel of any of 1-71 wherein the hydrogel is a first hydrogel, the hydrogel further comprising forming a second hydrogel in situ with a second agent in the second hydrogel, the second agent optionally having a low solubility in water.

73. The hydrogel of 72 wherein the first agent and the second agent have the same active ingredient.

74. The hydrogel of 72 or 73 wherein the first agent and the second agent comprise different enantiomers, salts, or free bases.

75. The hydrogel of 72 or 73 wherein the first agent and the second agent have identical chemical structures.

76. The hydrogel of any of 72-75, with the first hydrogel releasing the agent more quickly than the second hydrogel.

77. The hydrogel of any of 72-76 with the first hydrogel having a larger surface area than the second hydrogel.

78. The hydrogel of any of 72-77 with the first hydrogel providing a faster rate of diffusion for the agent relative to the second hydrogel.

79. The hydrogel of any of 72-78 wherein the first agent and the second agent are different chemical moieties.

80. The hydrogel of any of 72-79 wherein the hydrogel is formed by combining a first precursor and a second precursor that react with each other to form the hydrogel.

81. The hydrogel of 80 wherein the hydrogel is formed without covalent crosslinks between the first precursor and the second precursor.

82. The hydrogel of any of 1-81 wherein the hydrogel is formed by combining a first precursor comprising nucleophilic groups with a second precursor comprising electrophilic groups to form covalent crosslinks by reaction of the nucleophilic groups with the electrophilic groups to form the hydrogel.

83. The hydrogel of any of 80-82 comprising injecting an aqueous mixture of the precursors to the site.

84. The hydrogel of any of 80-83 wherein the first precursor and the second precursor are hydrophilic.

85. The hydrogel of any of 80-84 wherein the first precursor and/or the second precursor comprise poly(ethylene) glycol repeats.

86. The hydrogel of any of 51-85 further comprising hyaluronic acid or hydrophilic polymers that do not form part of a matrix of the hydrogel.

87. The hydrogel of any of 51-86 comprising activating a precursor to form the hydrogel.

88. The hydrogel of any of 51-87 comprising mixing a plurality of precursors to start a chemical reaction between the plurality of precursors, with the plurality of precursors reacting with each other to form the hydrogel.

89. The hydrogel of any of 82-88 wherein the precursors are activated and/or mixed before, after, or during placement at the site.

90. The hydrogel of any of 81-88 further comprising a buffering agent.

91. The hydrogel of 90 wherein the buffering agent is a solid.

92. The hydrogel of 91 wherein the solid is disposed in an applicator for placing a hydrogel precursor at the site, with the precursor contacting the solid as the precursor is passed through the applicator.

93. The hydrogel of 91 or 92 wherein the solid is disposed in a lumen of the applicator that receives the precursor, is disposed in a hub of a needle, is disposed in a syringe, or is a pellet for placement in an/the applicator.

94. The hydrogel of any of 90-93 wherein the buffering agent comprises a phosphate, bicarbonate, or carbonate.

95. The hydrogel of any of 1-94 wherein the site and/or the tissue is a tumor, a damaged tissue, a diseased tissue, an infected tissue, an organ, a vasculature, an adventitia, an artery, a vein, or a nerve.

96. The hydrogel of any of 1-95 wherein the hydrogel is elongate, spheroidal, spherical, essentially spherical, ellipsoidal, cylindroid, essentially cylindroid, discoidal, or essentially discoidal.

97. The hydrogel of any of 1-96 wherein the agent is delivered at an effective amount or a calculated effective amount.

98. A use of the method or the hydrogel of any of 1-97.

99. A use of the method or the hydrogel of any of 1-97 for delivery of an effective amount of an agent. For instance, to treat a disease. For instance, to treat a disease of an eye as in any of 1-97.

100. A use of the method or the hydrogel of any of 1-97 for delivery of an effective amount of an agent to a tissue. For instance, to treat a disease.

101. An agent as set forth in any of 1-97 for treatment of a condition as set forth in any of 1-97. A use of an agent set forth herein or in any of 1-97 for treatment of a condition as set forth herein or in any of 1-97.

102. A kit combining a precursor and an agent from any of 1-101 or as set forth herein.

103. A kit for any method, use, or agent as set forth in any of 1-101, the kit combining a precursor and an agent.

104. A process of making a kit of any of 102-103.

105. A process of making a hydrogel of any of 51-97.

106. The process of 105 comprising a method of any of 1-49.

107. The process of 105 comprising preparing a precursor as set forth herein or in any of 1-97.

108. The process of 107 further comprising adding an agent to the precursor.

109. A process of making a medicament comprising making a hydrogel of any of 51-97 or comprising a method of any of 1-50.

110. The process of 109 for treating a condition, e.g., a condition as set forth herein or in any of 1-97.

Many embodiments have been set forth herein. In general, components of the embodiments may be mixed-and-matched with each other as guided for the need to make functional embodiments. Patent application, patents, journal articles, and publications set forth herein are hereby incorporated by reference herein; in case of conflict, the instant specification controls.

The invention claimed is:

1. A method of delivering a therapeutic agent to a tissue comprising combining a first precursor and a second precursor that react with each other in presence of a therapeutic agent to form a covalently crosslinked hydrogel in situ in an eye with the therapeutic agent dispersed in the hydrogel, all of the agent being directly disposed in the hydrogel and having a low solubility in water, and with the hydrogel being formed with a spacing between crosslinks that allows diffusion of the agent through the hydrogel, wherein the hydrogel essentially persists at least until the agent has been essentially released.

2. The method of claim 1 with the agent being suspended in the hydrogel.

3. The method of claim 1 wherein the agent is released to provide an effective concentration of the agent in an eye over a period of time.

4. The method of claim 3 wherein the period of time starts after the formation of the hydrogen and ends at 2-36 months.

5. The method of claim 4 wherein, after the period of time, the hydrogel releases a further amount of the agent that is non-toxic.

6. The method of claim 1 wherein the hydrogel is water-degradable, as measurable by the hydrogel being dissolvable in vitro in an excess of water by degradation of water-degradable groups.

7. The method of claim 1 wherein the hydrogel is formed at an intravitreal site.

8. The method of claim 1 wherein the agent is for treatment of a back of the eye disease.

9. The method of claim 8 wherein the back of the eye disease is choroidal neovascularization (CNV), age-related macular degeneration (AMD) cystoid macular edema (CME), diabetic macular edema (DME), posterior uveitis, and diabetic retinopathy, or glaucoma.

10. The method of claim 1 wherein the agent
comprises anti-VEGF,
blocks VEGFR1, blocks VEGFR2, blocks VEGFR3, anti-PDGF, anti-PDGF-R blocks PDGFRβ,
comprises an anti-angiogenic agent, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, a tyrosine kinase inhibitor (TKI), Imatinibn gefinitib, toceranib, Erlotinib, Lapatinib, Nilotinib, Bosutinib Neratinib, lapatinib, Vatalanib,
comprises low-soluble prostaglandin analogues for glaucoma, nepafenac, macrolides, rapamycin, sirolimus, tacrolimus, or
serves to block mTOR receptors for AMD and/or CNV.

11. The method of claim 1 wherein the first precursor and the second precursor are hydrophilic.

12. The method of claim 1 wherein the hydrogel is essentially spherical, essentially discoidal, or essentially cylindroid.

13. The method of claim 11 wherein the first precursor is a multifunctional precursor that comprises a plurality of first functional groups and the second precursor is a multifunctional precursor that comprises a plurality of second functional groups, with the first functional groups and the second functional groups reacting with each other to form covalent bonds for covalently crosslinking the hydrogel.

14. The method of claim 13 wherein the first functional groups comprise electrophilic functional groups and the second functional groups comprise nucleophilic functional groups.

15. The method of claim 14 wherein the first precursor comprises a polyethylene glycol polymer.

16. The method of claim 15 wherein the polyethylene glycol polymer is a branched polymer.

17. The method of claim 16 wherein the first precursor has a number average molecular weight from 5000 to 50,000 Daltons.

18. The method of claim 17 wherein the second precursor comprises a branched polyethylene glycol having 4-16 arms.

19. The method of claim 17 wherein the second precursor is a dilysine, a trilysine, or tetralysine.

20. The method of claim 13 wherein the first multifunctional precursor has arms with a number average molecular weight of about 5000 Daltons each.

21. The method of claim 13 wherein the first precursor and the second precursor are each a four armed branched polyethylene glycol having a number average molecular weight of about 20,000.

* * * * *

UNITED STATES PATENT AND TRADEMARK OFFICE
CERTIFICATE OF CORRECTION

PATENT NO. : 11,369,591 B2
APPLICATION NO. : 15/152739
DATED : June 28, 2022
INVENTOR(S) : Jarrett et al.

It is certified that error appears in the above-identified patent and that said Letters Patent is hereby corrected as shown below:

On the Title Page

Column 1, Item (56), under "U.S. PATENT DOCUMENTS", Line 1, delete "Ztes" and insert -- Etes --, therefor.

On Page 2, Column 2, Item (56), under "OTHER PUBLICATIONS", Line 4, delete ""Biodegrable" and insert -- "Biodegradable --, therefor.

On Page 2, Column 2, Item (56), under "OTHER PUBLICATIONS", Line 16, delete "Oneology," and insert -- Oncology, --, therefor.

In the Claims

In Column 56, Claim 10, Line 41, delete "Imatinibn gefinitib," and insert -- imatinib, gefitinib, --, therefor.

Signed and Sealed this
Twenty-seventh Day of September, 2022

Katherine Kelly Vidal
*Director of the United States Patent and Trademark Office*